United States Patent
Nishigaki

(10) Patent No.: US 12,127,878 B2
(45) Date of Patent: Oct. 29, 2024

(54) ULTRASOUND DIAGNOSTIC DEVICE AND STORAGE MEDIUM

(71) Applicant: Konica Minolta, Inc., Tokyo (JP)

(72) Inventor: Morio Nishigaki, Fujisawa (JP)

(73) Assignee: KONICA MINOLTA, INC., Tokyo (JP)

( * ) Notice: Subject to any disclaimer, the term of this patent is extended or adjusted under 35 U.S.C. 154(b) by 4 days.

(21) Appl. No.: 17/662,946

(22) Filed: May 11, 2022

(65) Prior Publication Data
US 2022/0370032 A1 Nov. 24, 2022

(30) Foreign Application Priority Data
May 20, 2021 (JP) .................................. 2021-085042

(51) Int. Cl.
*A61B 8/08* (2006.01)
*A61B 8/00* (2006.01)
*A61B 8/14* (2006.01)

(52) U.S. Cl.
CPC ............... *A61B 8/085* (2013.01); *A61B 8/14* (2013.01); *A61B 8/4254* (2013.01); *A61B 8/4494* (2013.01); *A61B 8/463* (2013.01); *A61B 8/465* (2013.01); *A61B 8/466* (2013.01)

(58) Field of Classification Search
CPC ......... A61B 8/085; A61B 8/14; A61B 8/4254; A61B 8/4494; A61B 8/463; A61B 8/465; A61B 8/466; A61B 8/5207; A61B 8/54
See application file for complete search history.

(56) References Cited

U.S. PATENT DOCUMENTS

| | | | | |
|---|---|---|---|---|
| 6,375,617 B1* | 4/2002 | Fraser | ................. | G01S 15/8979 600/443 |
| 10,123,769 B2* | 11/2018 | Yamamoto | ............... | A61B 8/14 |
| 2006/0079777 A1* | 4/2006 | Karasawa | ................ | A61B 8/14 600/443 |
| 2008/0319317 A1* | 12/2008 | Kamiyama | ............ | A61B 8/463 600/443 |
| 2009/0099454 A1* | 4/2009 | Yao | ..................... | G01S 15/8925 600/459 |
| 2009/0306511 A1* | 12/2009 | Yamagata | ........... | G01S 7/52085 600/447 |

(Continued)

FOREIGN PATENT DOCUMENTS

JP 2007-319492 A 12/2007

*Primary Examiner* — Adil Partap S Virk
(74) *Attorney, Agent, or Firm* — LUCAS & MERCANTI, LLP

(57) ABSTRACT

An ultrasound diagnostic device including: an ultrasound probe that includes: multiple vibrators that are arrayed to be multiple rows in a long axis direction, the rows being arranged in a short axis direction, and that transmit and receive ultrasonic waves; a switching element that switches on and off of input of a drive signal to a vibrator in each of the rows and output of a received signal; an ultrasound image generator that generates ultrasound image data of a tomographic plane for each of the rows based on the received signal that is received by the vibrator corresponding to each of the rows via switching of the switching element; and a three-dimensional image generator that generates three-dimensional image data from the generated ultrasound image data of the multiple rows.

14 Claims, 19 Drawing Sheets

(56) References Cited

U.S. PATENT DOCUMENTS

| | | | |
|---|---|---|---|
| 2010/0056921 A1* | 3/2010 | Rafter | A61B 8/06 600/447 |
| 2012/0087564 A1* | 4/2012 | Tsujita | A61B 8/5223 382/131 |
| 2012/0179043 A1* | 7/2012 | Kim | G01S 7/52017 600/447 |
| 2014/0330126 A1* | 11/2014 | Kang | G10K 11/34 600/447 |
| 2015/0164473 A1* | 6/2015 | Kim | A61B 8/4494 600/443 |
| 2015/0196273 A1* | 7/2015 | Yamamoto | G01S 7/52047 600/447 |
| 2015/0245819 A1* | 9/2015 | Yoshiara | A61B 8/0866 600/431 |
| 2015/0359512 A1* | 12/2015 | Boctor | G01S 15/8997 600/447 |
| 2016/0058418 A1* | 3/2016 | Lee | A61B 8/465 600/437 |
| 2017/0236248 A1* | 8/2017 | Pintoffl | A61B 8/4461 |
| 2019/0029644 A1* | 1/2019 | Nishigaki | G01S 7/5208 |
| 2019/0216429 A1* | 7/2019 | Sakai | A61B 8/4461 |
| 2021/0278530 A1* | 9/2021 | Haque | G01S 7/5208 |
| 2022/0096053 A1* | 3/2022 | Sethuraman | A61B 8/4488 |

* cited by examiner

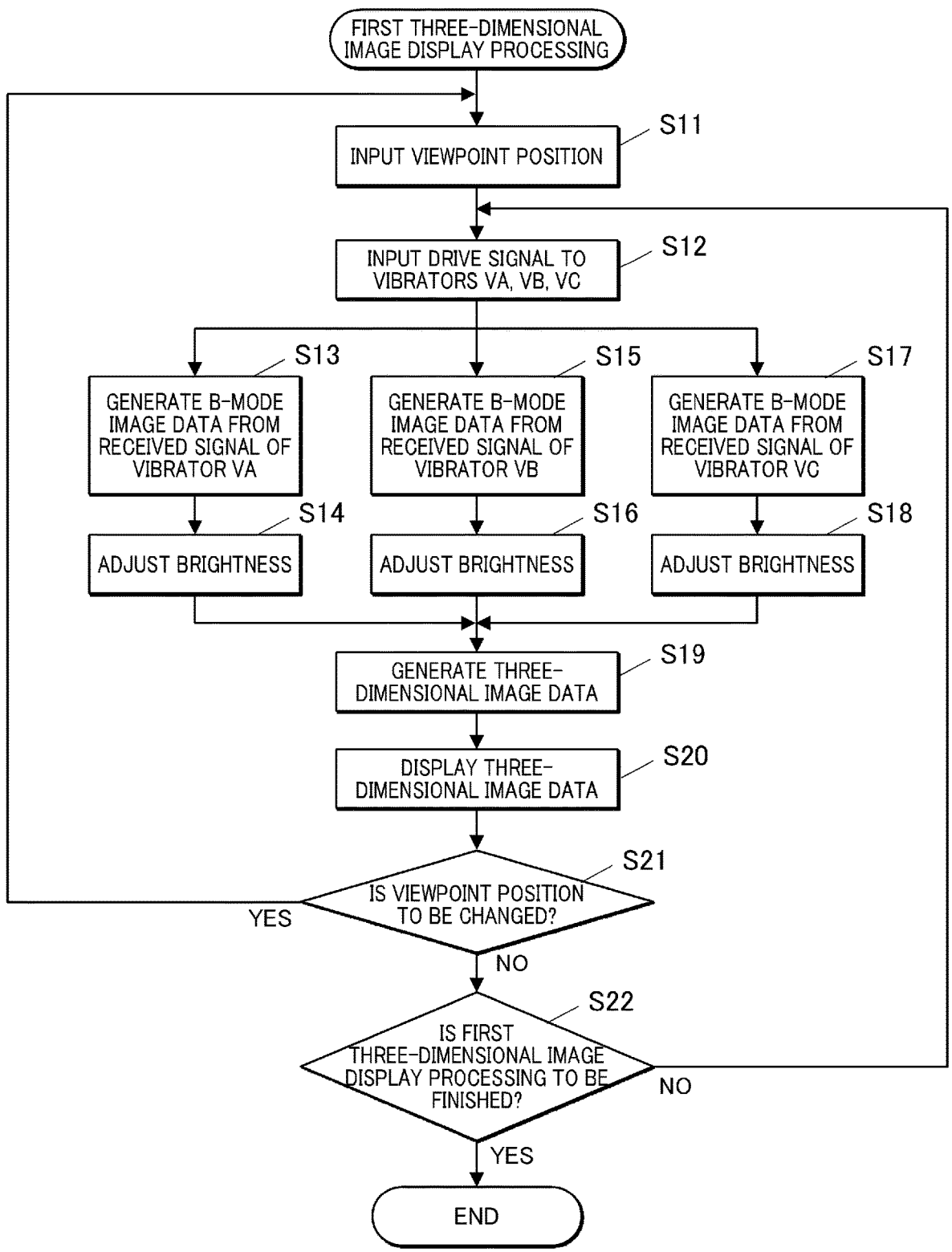

ULTRASOUND DIAGNOSTIC DEVICE AND STORAGE MEDIUM

CROSS-REFERENCE TO RELATED APPLICATIONS

The entire disclosure of Japanese Patent Application No. 2021-085042 filed on May 20, 2021 is incorporated herein by reference in its entirety.

BACKGROUND

Technological Field

The present invention relates to an ultrasound diagnostic device and a storage medium.

Description of the Related Art

Ultrasound diagnostic devices are widely used to examine the inside of a subject by emitting ultrasonic waves into the subject and receiving and analyzing the reflected waves. Since ultrasound diagnostic devices can examine subjects nondestructively and noninvasively, they are widely used for medical purposes, inspection inside building structures, and various other applications.

There are also known ultrasound diagnostic devices including a sensor that detects movement information of an ultrasound probe and creates and displays a stereoscopic image from a position of the ultrasound probe calculated from the information by the sensor and a plurality of ultrasound tomographic images created over time based on received signals of the ultrasound probe. For example, in JP 2007-319492A, an acceleration sensor is used to detect the movement information, and the examiner moves the ultrasound probe manually at a constant speed in the depth direction (perpendicular to the running direction of the array vibrators) with reference to the displayed acceleration to create a stereoscopic image.

SUMMARY

However, with the ultrasound diagnostic device described in JP 2007-319492A, it was difficult to move the probe accurately and with constant velocity in the movement using the hand, and even with reference to acceleration, it was not easy to identify the exact position, especially the minute position, and there was a risk of creating a stereoscopic image with tomographic images at positions that were not appropriate (not evenly spaced) in the depth direction.

An object of the present invention is to generate three-dimensional image data having ultrasound images of appropriate positions in the depth direction.

To achieve at least one of the abovementioned objects, according to an aspect of the present invention, an ultrasound diagnostic device reflecting one aspect of the present invention is an ultrasound diagnostic device including: an ultrasound probe that includes: multiple vibrators that are arrayed to be multiple rows in a long axis direction, the rows being arranged in a short axis direction, and that transmit and receive ultrasonic waves; a switching element that switches on and off of input of a drive signal to a vibrator in each of the rows and output of a received signal; an ultrasound image generator that generates ultrasound image data of a tomographic plane for each of the rows based on the received signal that is received by the vibrator corresponding to each of the rows via switching of the switching element; and a three-dimensional image generator that generates three-dimensional image data from the generated ultrasound image data of the multiple rows.

To achieve at least one of the abovementioned objects, according to another aspect of the present invention, a storage medium reflecting one aspect of the present invention is a non-transitory computer-readable storage medium storing a program for a computer of an ultrasound diagnostic device including an ultrasound probe that includes: multiple vibrators that are arrayed to be multiple rows in a long axis direction, the rows being arranged in a short axis direction, and that transmit and receive ultrasonic waves; and a switching element that switches on and off of input of a drive signal to a vibrator in each of the rows and output of a received signal, the program causing the computer of the ultrasound diagnostic device to perform ultrasound image generating that is generating ultrasound image data of a tomographic plane for each of the rows based on the received signal that is received by the vibrator corresponding to each of the rows via switching of the switching element; and three-dimensional image generating that is generating three-dimensional image data from the generated ultrasound image data of the multiple rows.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 6 is a flowchart showing first three-dimensional image display processing;

DETAILED DESCRIPTION OF EMBODIMENTS

Hereinafter, first and second embodiments and first to third modification examples according to the present invention will be described in detail in order with reference to the drawings. However, the scope of the invention is not limited to the disclosed embodiments or illustrated examples.

First Embodiment

With reference to FIGS. 1 to 14C, the first embodiment according to the present invention will be described.

Figure 1:
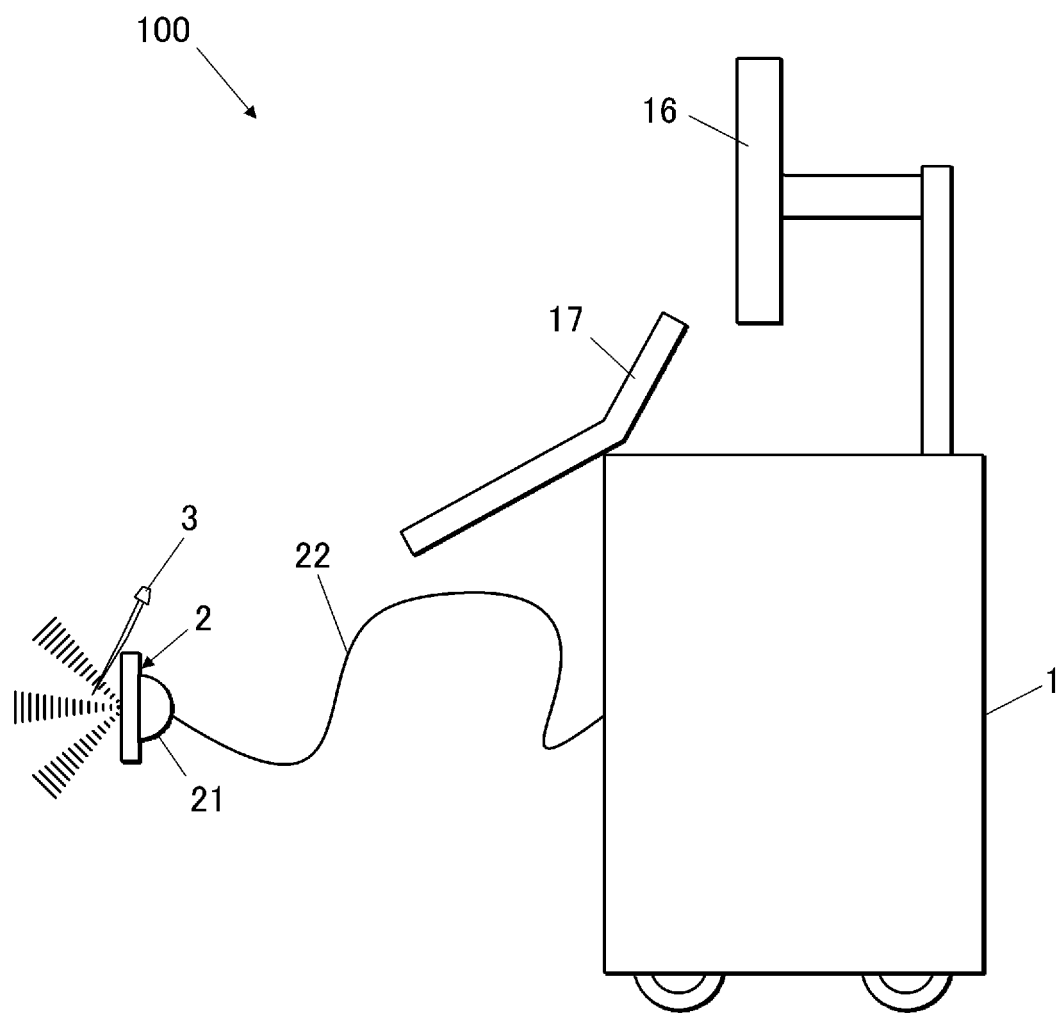
FIG. 1 is an overall view of the ultrasound diagnostic device of the first embodiment of the present invention.
Figure 2:
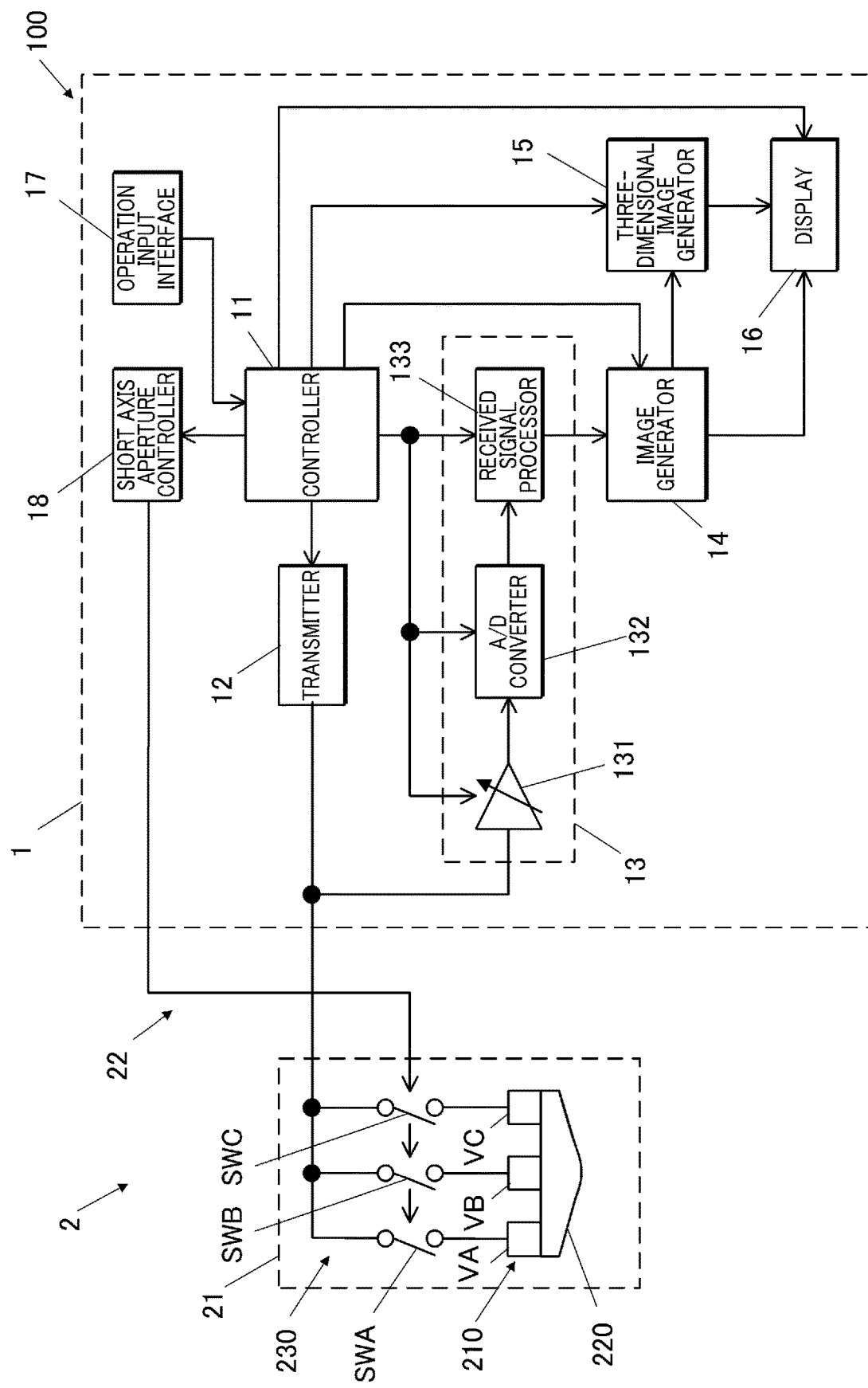
FIG. 2 is a block diagram showing the internal structure of the ultrasound diagnostic device of the first embodiment.
Figure 3:
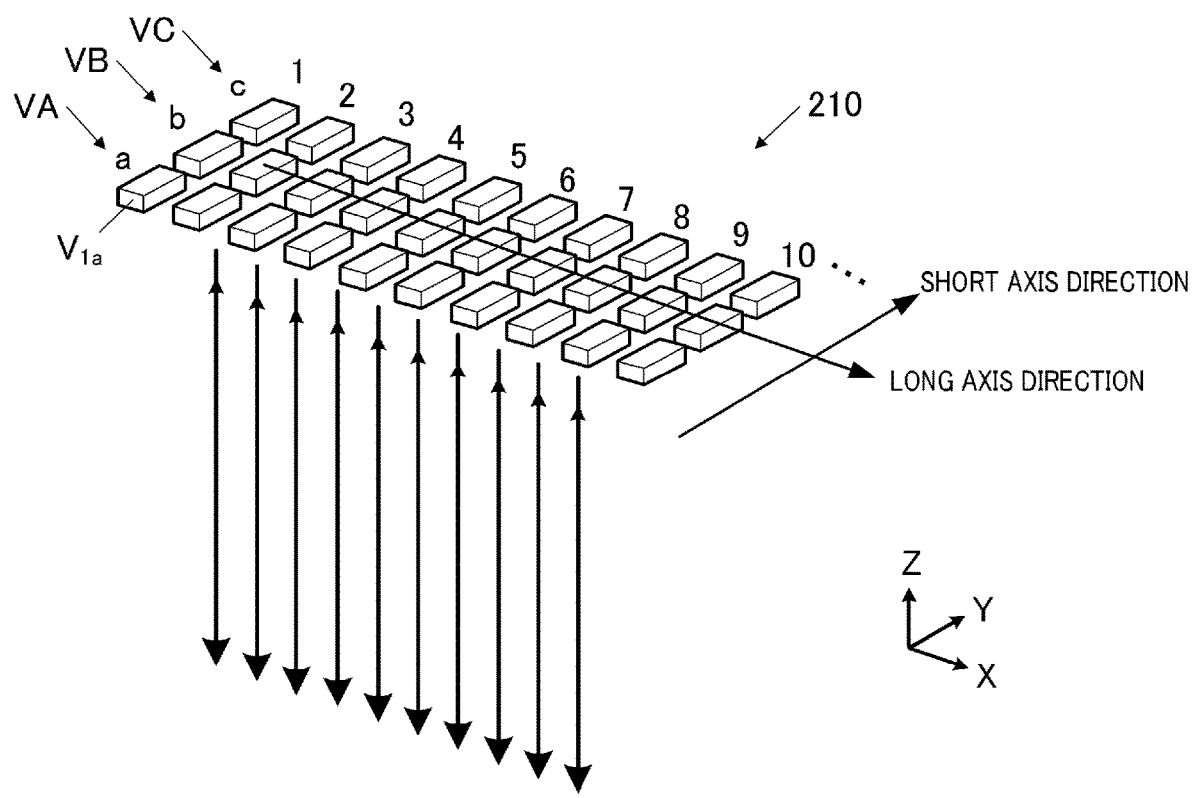
FIG. 3 is a view showing an example of an array of vibrators in an ultrasound probe.
Figure 4:
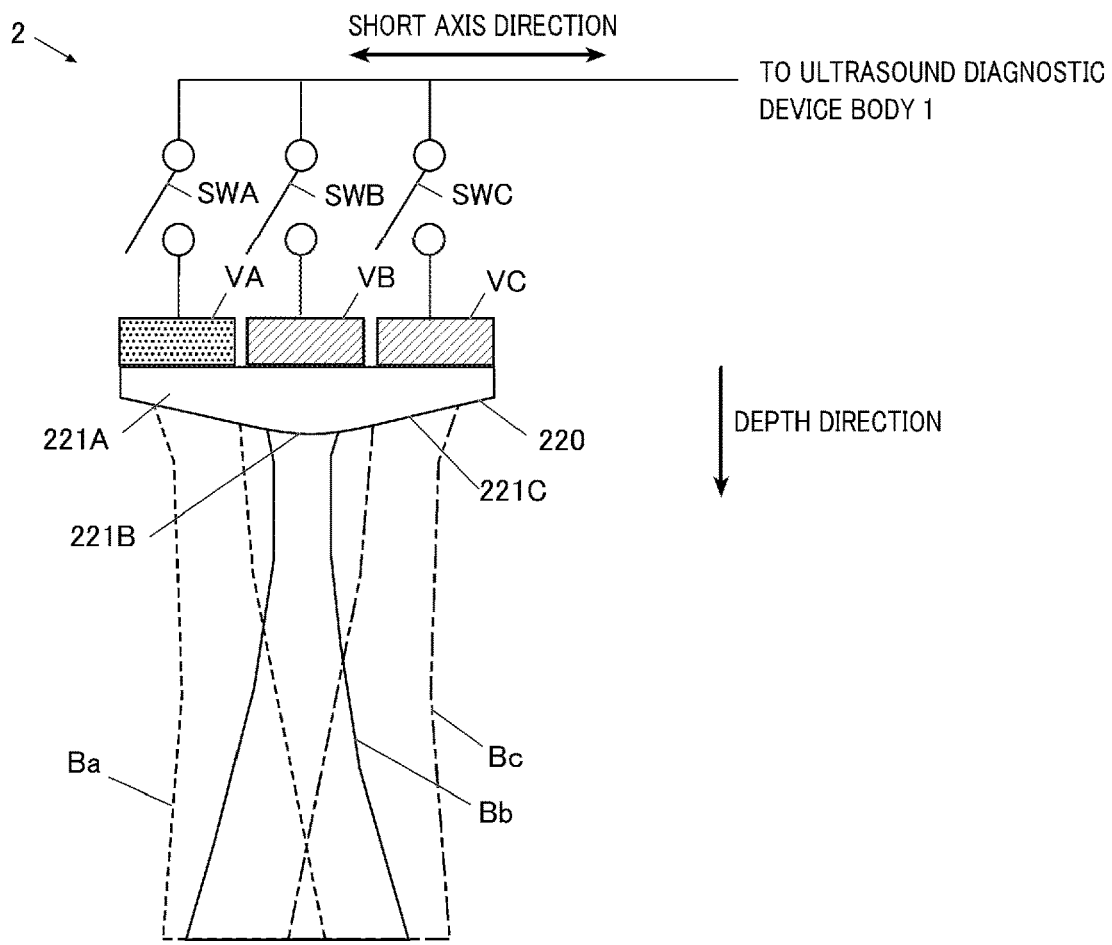
FIG. 4 is a view showing a schematic configuration of the ultrasound probe in the short axis direction and the three ultrasonic beams.
Figure 5A:
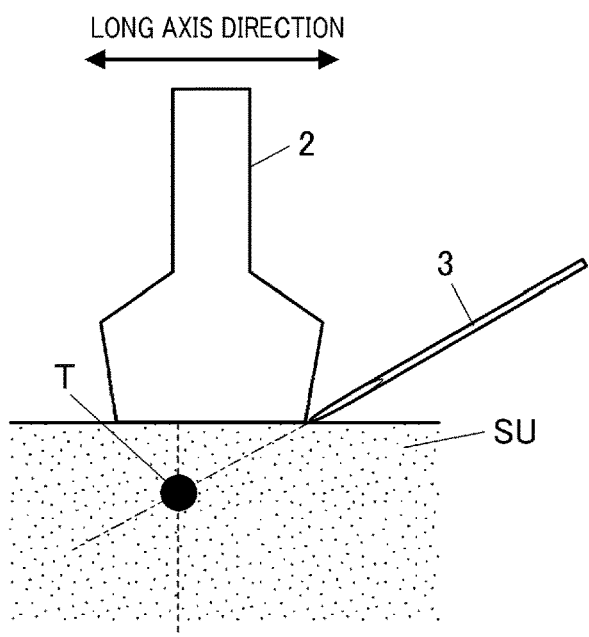
FIG. 5A is a schematic diagram showing the in-plane approach in ultrasound-guided puncture.
Figure 5B:
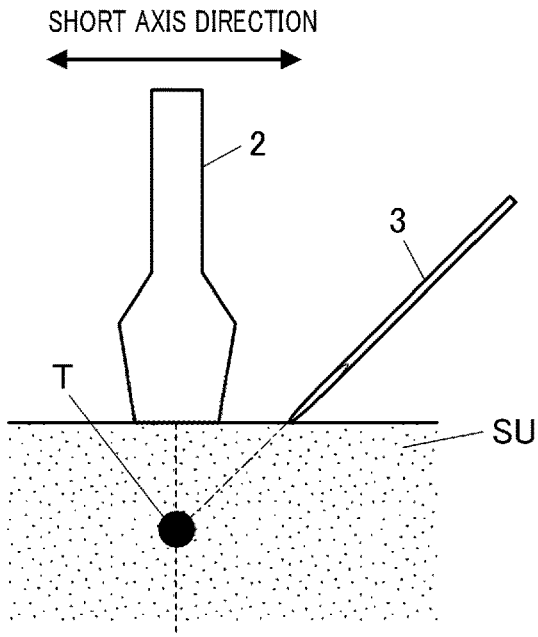
FIG. 5B is a schematic diagram showing the out-of-plane approach in ultrasound-guided puncture.

With reference to FIGS. 1 to 5B, the device configuration of ultrasound diagnostic device 100 in the embodiment will be described. FIG. 1 is an overall view of the ultrasound diagnostic device 100 of the embodiment. FIG. 2 is a block diagram showing the internal structure of the ultrasound diagnostic device 100 of the embodiment. FIG. 3 is a view showing an example of an array of vibrators 210 in an ultrasound probe 2. FIG. 4 is a view showing a schematic configuration of the ultrasound probe 2 in the short axis direction and the three ultrasonic beams Ba, Bb and Bc. FIG. 5A is a schematic diagram showing the in-plane approach in ultrasound-guided puncture. FIG. 5B is a schematic diagram showing the out-of-plane approach in ultrasound-guided puncture.

The ultrasound diagnostic device 100 of the embodiment is installed in a hospital or other medical facility to generate and display ultrasound image data from the subject, the patient's living body. In particular, the ultrasound diagnostic device 100 generates the ultrasound image data (three-dimensional image data) of the pseudo three-dimensional image to visualize (observe) the puncture needle 3, which is a treatment tool, and the subject's tumor or other tissue, as a recognition object.

As shown in FIG. 1, the ultrasound diagnostic device 100 comprises an ultrasound diagnostic device body 1, an ultrasound probe 2 connected to the ultrasound diagnostic device body 1, and the puncture needle 3 which is a treatment tool as the recognition object.

The puncture needle 3 has a hollow long needle shape and is inserted into the subject at an angle determined by the operator, such as a physician, freehand The puncture needle 3 can be replaced with one of appropriate thickness, length, and tip shape according to the site (target) to be collected of the subject, such as the patient, or the type and amount of the drug to be injected. The ultrasound diagnostic device 100 may be configured with a mounting portion as an attachment that guides the puncture needle 3 in the puncture direction, or a guide portion fixed to the ultrasound probe 2 to guide the puncture needle 3 in the puncture direction.

The ultrasound diagnostic device body 1 has the display 16 and the operation input interface 17. As shown in FIG. 2, in addition to the above, the ultrasound diagnostic device body 1 is also equipped with the controller 11 (hardware processor), the transmitter 12, the receiver 13, the image generator 14 as ultrasound image generator, the three-dimensional image generator 15, the short axis aperture controller 18, etc. The controller 11 outputs drive signals to the ultrasound probe 2 to output ultrasonic waves based on external input operations to input devices such as the keyboard and mouse on the operation input interface 17, acquires the received signals pertaining to ultrasound reception from the ultrasound probe 2, performs various processing, and displays the results of ultrasound images, etc. on the display screen of the display 16, etc., as necessary.

The ultrasound probe 2 functions as an acoustic sensor that transmits and emits ultrasonic waves (in this case, about 1 to 30 MHz) to the subject, such as a living body, and receives the reflected waves (echoes) of the emitted ultrasonic waves that are reflected by the subject and converts them into electrical signals.

The ultrasound probe 2 has the ultrasound probe body 21 and the cable 22. The ultrasound probe body 21 is the header that transmits and receives ultrasonic waves to the subject. The ultrasound probe body 21 has a plurality of vibrators 210 which transmit and receive ultrasonic waves, the acoustic lens 220, and a plurality of switching elements 230 corresponding to the respective vibrators 210. The ultrasound probe 2 emits ultrasonic waves from the outside (body surface) into the subject and receives the reflected waves, but is not limited to this. The ultrasound probe 2 can be of a size and shape to be inserted into the interior of digestive tracts, blood vessels or other organs, or into a body cavity. The operator operates the ultrasound diagnostic device 100 by causing the ultrasound probe 2's transmitting and receiving surfaces of ultrasonic waves, i.e., the surfaces in the direction of emission of ultrasonic waves from the vibrators 210 to contact the subject at a specified pressure and operates the ultrasound diagnostic device 100, to perform ultrasound diagnosis.

The number of vibrators 210 can be set arbitrarily. In the embodiment, the ultrasound probe 2 uses a linear scanning electron scanning probe, but any electronic or mechanical scanning method can be used, and any of linear, sectoral, or convex scanning methods can also be used.

The vibrators 210 are a plurality of vibrators equipped with piezoelectric bodies and piezoelectric elements having electrodes at both ends where electric charges appear due to deformation (expansion and contraction) of the piezoelectric bodies. In current ultrasound diagnostic devices, piezoelectric elements are usually used to convert between electrical signals and ultrasonic waves signals, but the embodiment is not limited to this type of element.

As shown in FIG. 3, in the ultrasound diagnostic device 100, the vibrators 210 are multiple vibrators arranged in a matrix within a two-dimensional plane (a plane in the embodiment, but it does not have to be a plane) defined by a predetermined lateral direction (scanning direction) and an elevation direction orthogonal to the lateral direction. Usually, the number of arrays of the vibrators 210 in the lateral direction is greater than the number of arrays of the vibrators 210 in the elevation direction, with the lateral direction being the long axis direction and the elevation direction being the short axis direction. The vibrators 210 have a vibrator group of three rows of vibrators in the short axis direction (rows a, b, and c), and each row has multiple columns (columns 1, 2 . . . ) of vibrators arrayed in the long axis direction. Here, the vibrator group in row a is expressed as vibrator VA for convenience, and similarly, the vibrator groups in rows b and c are expressed as vibrators VB and VC. One vibrator in column x and row y is represented as vibrator Vxy. As shown in FIG. 3, the three-dimensional X, Y, and Z axes are taken, with the X axis as the long axis, the Y axis as the short axis, and the axis perpendicular to the X axis and Y aix is the Z axis.

When generating B (Brightness) mode image data as a normal tomographic image as the ultrasound image data of the tomographic plane, for example, ultrasonic waves are transmitted and received while sequentially shifting the vibrators driven in the long axis direction using the vibrator VB in row b.

When voltage pulses are supplied to each of the plurality of the vibrators 210 as a drive signal, the piezoelectric body of the vibrator to which the voltage pulse is supplied deforms (expands and contracts) in response to the electric field generated in the piezoelectric body, and ultrasonic waves are emitted. The emitted ultrasonic waves are emitted in a position and direction according to the position and direction of the vibrators 210 in the predetermined number of vibrator rows to which the voltage pulses are supplied, the direction of convergence of the emitted ultrasonic waves, and the magnitude of timing deviation (delay). When ultrasonic waves (reflected waves at the subject) in a predetermined frequency band are incident on the vibrators 210, the sound pressure causes the thickness of the piezoelectric body to fluctuate (vibrate), generating an electric charge corresponding to the amount of fluctuation, which is converted into an electrical signal corresponding to the amount of charge and output as a received signal.

As shown in FIG. 2 and FIG. 4, the acoustic lens 220 is an aspherically shaped lens that focuses the ultrasonic beams (transmitted ultrasonic waves) emitted from the vibrators 210 (vibrators VA, VB, VC). The acoustic matching layer between the acoustic lens 220 and the vibrators 210 and the backing material on the opposite side of the vibrators 210 from the direction of emission of ultrasonic waves are omitted from the figure.

The acoustic lens 220 has a lens section 221A through which the ultrasonic beam Ba emitted from the vibrator VA passes, a lens section 221B through which the ultrasonic beam Bb emitted from the vibrator VB passes, and a lens section 221C through which the ultrasonic beam Bc emitted from the vibrator VC passes.

The switching elements 230 are a plurality of switches that can independently turn on and off the drive signal input to each of the vibrators of vibrators 210 from the transmitter 12 and output of the received signal, via the cable 22, according to the control from the short axis aperture controller 18. The switching elements 230 include the switching elements SWA, SWB, and SWC. The switching elements SWA are a plurality of switches corresponding to respective vibrators of vibrator VA. The switching elements SWB are a plurality of switches corresponding to respective vibrators of vibrator VB. The switching elements SWC are a plurality of switches corresponding to respective vibrators of vibrator VC.

The cable 22 has a plug connector (not shown) at one end that is connected to the receptacle connector (not shown) of the ultrasound diagnostic device body 1 and is electrically connected to the ultrasound probe body 21 at the other end. The ultrasound probe body 21 is removable from the ultrasound diagnostic device body 1 by means of the cable 22.

Returning to FIG. 2, the controller 11 consists of a CPU (Central Processing Unit), an HDD (hard disk drive) and RAM (Random Access Memory). The CPU reads the various programs stored in the HDD and loads them into RAM, and then comprehensively controls the operation of each part of the ultrasound diagnostic device 100 according to said programs. The HDD stores control programs and various processing programs that operate the ultrasound diagnostic device 100, as well as various setting data. The HDD stores, in particular, the first three-dimensional image display program for performing the first three-dimensional image display processing described below. These programs and setting data may be stored in auxiliary storage devices using non-volatile memory such as ROM (Read Only Memory) or flash memory including SSD (Solid State Drive), for example, in addition to HDD. RAM is a volatile memory such as SRAM (Static RAM) or DRAM (Dynamic RAM) that provides the CPU with a working memory space and stores temporary data.

The transmitter 12 generates a drive signal to supply to the ultrasound probe 2 and outputs it to the ultrasound probe 2, using power supply power from the transmitter power supply (not shown), which outputs power supply power according to the control signal input from the controller 11, causing the ultrasound probe 2 to transmit ultrasonic waves. The transmitter 12 is equipped with, for example, a clock generation circuit, a pulse width setting section, a pulse generation circuit, and a delay circuit. The clock generation circuit is a circuit that generates a clock signal that determines the timing and frequency of pulse signal transmission. The pulse width setting section sets the waveform (shape), voltage amplitude and pulse width of the transmission pulses to be output from the pulse generation circuit. The pulse generator circuit generates a transmission pulse as a drive signal based on the settings of the pulse width setting section and outputs it to different wiring paths for each of the individual vibrators 210 of the ultrasound probe 2. The delay circuit counts the clock signal output from the clock generation circuit, and when the set delay time elapses, it causes the pulse generation circuit to generate a transmission pulse for output to each wiring path.

In response to the drive signal from the transmitter 12, ultrasonic waves are emitted from the vibrators 210 of the ultrasound probe 2 to the subject, such as the patient's living body. The reflected ultrasonic waves (echoes) reflected at the subject are received by the vibrators 210 to generate a received signal as an electrical signal.

The ultrasound diagnostic device 100 has two image modes: B-mode, which generates B-mode image data of a tomographic image representing the received signal of ultrasonic waves of the subject in terms of brightness, and the color Doppler mode, which generates color flow image data of the color flow image as the ultrasound image data of the tomographic plane that represents the blood flow of the subject in color. In the B-mode, the transmitter 12 emits the ultrasonic wave once per frame at the same position on the subject, and the received signal corresponding to the ultrasonic wave emitted once is generated over multiple positions to produce B-mode image data. In the color Doppler mode, the ultrasonic wave is emitted at the same position of the subject within the ROI (Region Of Interest), which was input from the operator via the operation input interface 17, multiple times (repetition number n) for each frame by the transmitter 12, and the received signals corresponding to the multiple ultrasonic waves are acquired by the receiver 13 over multiple positions, the velocity components of blood flow, etc. are calculated, and color flow image data of the ROI is generated. The color flow image data of the ROI and the B-mode image data are superimposed and displayed.

The ultrasound diagnostic device 100 may be configured to generate the ultrasound image data in other image modes besides B-mode and color Doppler mode, such as M (Motion) mode and pulsed Doppler mode.

The receiver 13 is a circuit that acquires the received signal input from the ultrasound probe 2 under the control of the controller 11. The receiver 13 has, for example, a variable gain amplifier 131, an A/D (Analog to Digital) converter 132, and a received signal processor 133. The variable gain amplifier 131 is a circuit that amplifies the received signals corresponding to the ultrasonic waves received by each of the vibrators 210 of the ultrasound probe 2 at a set amplification ratio, according to the control of the controller 11. The A/D converter 132 is a circuit that converts the received signal amplified by the variable gain amplifier 131 into digital data at a predetermined sampling frequency according to the control of the controller 11. The received signal processor 133 is a circuit that, in accordance with the control of the controller 11, gives a delay time for each wiring path corresponding to each of the vibrators 210 to the received signal A/D-converted by the A/D converter 132 to adjust the time phase, and adds them together (phasing addition) to generate sound line data.

The image generator 14 generates the ultrasound image data for diagnosis based on the sound line data input from the receiver 13 according to the control of the controller 11. The image generator 14 detects the sound line data input from the receiver 13 in B-mode or color Doppler mode (envelope detection) to obtain a signal, and performs logarithmic amplification, filtering (e.g., low-frequency transmission, smoothing, etc.), enhancement, and other processing as necessary, and uses a brightness signal corresponding to the intensity of the signal to generate each frame image data (B-mode image data) for B-mode display as a tomographic image representing two-dimensional structures in a cross-section including the direction of the signal transmission (in the depth direction of the subject) and the scanning direction of the ultrasonic waves transmitted by the ultrasound probe 2 (lateral direction, long axis direction of the 2D array of the vibrators 210 in FIG. 3).

The image generator 14 generates color flow image data (color Doppler mode image data) of the ROI based on the ROI input from the operator via the operation input interface 17 in color Doppler mode, according to the sound line data input from the receiver 13. The image generator 14 has a corner turn control section, MTI (Moving Target Indicator) filter, correlation calculation section, data conversion section, noise reduction spatial filter section, inter-frame filter, and color flow image conversion section for the color Doppler mode.

The quadrature detection circuit calculates the phase difference between the acquired color Doppler mode received signal and the reference signal by quadrature detection of the color Doppler mode received signal input from the receiver 13 according to the control of the controller 11, and acquires (complex) Doppler signals I and Q. The corner turn control section, in accordance with the control of the controller 11, stores the Doppler signals I and Q input from the quadrature detection circuit in the memory (not shown) in an array for each same acoustic line (line), in the depth direction from the ultrasound probe to the subject and in the ensemble direction with n repetitions of ultrasonic waves transmission and reception, and reads the Doppler signals I and Q for each depth in the ensemble direction. The received signals (Doppler signals I, Q) contain a mixture of information on unwanted vessel wall and tissue (clutter components) in addition to the blood flow signal components necessary for generating color flow images. The MTI filter filters the Doppler signals I and Q input from the corner turn control section to remove clutter components according to the control of the controller 11.

The correlation calculation section is controlled by the controller 11, and, from the Doppler signal I, Q (complex Doppler signal z) filtered by the MTI filter, calculates the real part D and imaginary part N of the average value S (average value of phase difference vector) of the Doppler signal autocorrelation operation. The data conversion section calculates the blood flow velocity, power, and dispersion from the Doppler signals I and Q filtered by the MTI filter and the real part D and imaginary part N of the average value S of the Doppler signal autocorrelation calculation, according to the control of the controller 11. The noise reduction spatial filter section filters the power, blood flow velocity, and dispersion calculated by the data conversion section. The inter-frame filter filters the blood flow components in each frame of the color flow image so as to smooth the inter-frame changes and leave afterimages, corresponding to the display mode of the color Doppler mode that was operationally input at the operation input interface 17, out of the blood flow velocity, power, and dispersion filtered by the noise reduction spatial filter section. According to the control of the controller 11, the color flow image conversion section color maps the blood flow velocity, power, and dispersion filtered by the inter-frame filter, to be converted to a color flow image data of the ROI and generates the color flow image data of the ROI. For example, depending on the blood flow velocity, blood flow in the direction toward the ultrasound probe 2 is represented in red and blood flow away from the ultrasound probe 2 is represented in blue in the color flow image data.

The image generator 14 converts the generated B-mode image data into image signals and outputs them to the display 16 to display the B-mode image in the normal B-mode image (B-mode image that is not a three-dimensional image) display in B-mode. The image generator 14 superimposes the generated color flow image data of ROI and B-mode image data in the normal color flow image (color flow image that is not a three-dimensional image) display in color Doppler mode, converts them into image signals, and outputs them to the display 16 to display the superimposed image.

The image generator 14 outputs the generated B-mode image data to the three-dimensional image generator 15 in B-mode three-dimensional image display. The image generator 14 outputs the generated color flow image data of ROI and B-mode image data of to the three-dimensional image generator 15 in the color Doppler mode three-dimensional image display.

The three-dimensional image generator 15 combines the multiple pieces of ultrasound image data (three pieces of ultrasound image data generated by respectively using the vibrators VA, VB, and VC of different rows in the short axis direction of FIG. 3 (elevation direction)) input from the image generator 14 in accordance with the control of the controller 11 to generate three-dimensional image data. The three-dimensional image generator 15 generates B-mode three-dimensional image data by combining multiple pieces of B-mode image data in B-mode. The three-dimensional image generator 15 generates three-dimensional image data of B-mode images by combining multiple rows of B-mode image data in color Doppler mode and generates three-dimensional image data of color flow images by combining multiple rows of color flow image data.

The three-dimensional image generator 15 converts the generated B-mode image data into image signals and outputs them to the three-dimensional image generator 15 in B-mode three-dimensional image display. The image generator 14 converts the composite image of the generated color flow image data of ROI and B-mode image data into image signals and outputs them to the three-dimensional image generator 15 in the color Doppler mode three-dimensional image display.

The image generator 14 and the three-dimensional image generator 15 can perform image processing such as dynamic range adjustment and gamma correction for the display of the ultrasound image data. The image generator 14 and the three-dimensional image generator 15 can be configured with a dedicated CPU and RAM used to generate these images. Alternatively, in the image generator 14 and the three-dimensional image generator 15, the dedicated hardware configuration for image generation may be formed on a board (ASIC (Application-Specific Integrated Circuit), etc.), or formed by FPGA (Field Programmable Gate Array). Alternatively, the image generator 14 and the three-dimensional image generator 15 may be configured to perform processing related to image generation by the CPU and RAM of the controller 11.

The display 16 is the display device that has a display screen that uses any of the various display formats such as LCD (Liquid Crystal Display), organic EL (Electro-Luminescent) displays, inorganic EL displays, plasma displays, CRT (Cathode Ray Tube) displays. The display 16 displays various display information and the ultrasound image or the three-dimensional image of the ultrasound image, based on various display information input from the controller 11 and image signals input from the image generator 14 or the three-dimensional image generator 15, in accordance with control by the controller 11.

The operation input interface 17 includes encoders (rotary knobs), lever switches, joysticks, trackballs, keyboards, touchpads, and combinations of them, which are multi-function switches. The operation input interface 17 receives various operations from the operator, converts them into operation signals, and inputs them to the controller 11.

The display 16 and the operation input interface 17 may be integrated into the housing of the ultrasound diagnostic device body 1, or the display 16 and the operation input interface 17 may be externally attached via an RGB cable, USB (Universal Serial Bus) cable or HDMI (High-Definition Multimedia Interface) cable (registered trademark: HDMI). If the ultrasound diagnostic device body 1 has an operation input terminal or display output terminal, the display 16 and the operation input interface 17 may be used by connecting conventional operating and display peripherals to these terminals The short axis aperture controller 18 stores setting information for the transmission/reception sequence of the vibrators 210 for transmitting and receiving ultrasonic waves over the short axis direction (FIG. 3) of a two-dimensional array of the vibrators 210. The short axis aperture controller 18 switches on/off the switching element 230 corresponding to each of the vibrators 210 according to the setting information according to the control of the controller 11. The transmission/reception sequence of the vibrators 210 is described below. More specifically, the short axis aperture controller 18 controls the switching elements SWA, SWB, and SWC on and off as the switching elements 230 connected to the vibrators VA, VB, and VC in the respective rows of the short axis direction, according to the apertures of the vibrators 210 that transmit and receive ultrasonic waves.

In the ultrasound diagnostic device 100, though omitted in FIG. 2, as shown in FIG. 3, the vibrators 210 have multiple vibrators in the long axis direction and the short axis direction, the switching elements 230 have multiple switches corresponding to the respective multiple vibrators. The transmitter 12, the receiver 13, and the short axis aperture controller 18 correspond to each of said multiple vibrators or said multiple switches. This also applies to other embodiments of ultrasound diagnostic devices.

Referring now to FIGS. 3 through 5B, a more detailed configuration and operation of the ultrasound probe 2 is described. FIG. 5A is a schematic illustration of the in-plane approach in ultrasound-guided puncture; FIG. 5B is a schematic illustration of the out-of-plane approach in ultrasound-guided puncture.

Referring to FIG. 5A and FIG. 5B, description is made for the in-plane and out-of-plane approaches to puncture the puncture needle 3 as a recognition object under ultrasonic waves guidance.

As shown in FIG. 5A, the in-plane approach (parallel method) is the method of inserting puncture needle 3 parallel to the long axis direction toward the target T of tissue acquisition by puncture of the subject SU or the like. As shown in FIG. 5B, the out-of-plane approach (crossing method) is a method of inserting the puncture needle 3 in a direction orthogonal to the long axis direction toward the target T of the subject SU. The in-plane approach and out-of-plane approach are used differently depending on the use. The site to be punctured and the purpose of the puncture often determine which technique is used, but sometimes the choice is based on the operator's experience.

In the in-plane approach, when the puncture needle is inserted, the puncture needle is inserted into the subject SU from the long axis end of the ultrasound probe 2. The puncture is made deep within the tomographic plane formed by puncture needle of long axis of a row corresponding to the vibrator VB. If the puncture needle 3 deviates from the tomographic plane in the short axis direction, the puncture needle 3 will not be depicted by the conventional ultrasound diagnostic device.

In the out-of-plane approach, the puncture needle 3 is inserted obliquely into the subject SU from the short axis side of the ultrasound probe 2 and into the target T directly below the ultrasound probe. In the conventional out-of-plane approach, using a general ultrasound probe, the puncture needle 3 inserted into the body surface does not show up on the ultrasound image, even at a considerable depth. The image of the puncture needle appears in the ultrasound image for the first time in the immediate vicinity of the target T. This makes it difficult to know whether the puncture needle 3 is going in the right direction.

The embodiment captures the puncture needle 3 over a large area in both in-plane and out-of-plane approaches. Thus, at the same time, in addition to the frame of the ultrasound image by vibrator VB, the frame of the ultrasound image by vibrator VA and the frame of the ultrasound image by vibrator VC are obtained and the frame of the three-dimensional image is generated from these three frames of the ultrasound image.

As shown in FIG. 4, in the embodiment, the vibrators VA, VB, and VC are arranged so that the ultrasonic beams Ba, Bb, and Bc approximately do not overlap to a certain depth and there are no gaps between them.

The short axis width of the vibrator VB is wide enough to withstand normal ultrasonic scanning. The lens section 221B of the acoustic lens 220 covering the vibrator VB is assumed to have beam forming capability that can be used for normal ultrasonic scanning The short axis width of vibrators VA and VC can be narrower than that of vibrator VB, but the width large enough to obtain ultrasonic waves (echoes) reflected from the recognition object, such as needle 3. The lens sections 221A and 221C of the acoustic lens 220 covering the vibrators VA and VC should be aspherical in shape, such that the radius of curvature is larger than that of the lens section 221B, but an oblique flat shape can be used. The lens sections 221A, 221C of the acoustic lens 220 covering the vibrators VA, VC can be flat without being oblique, but it is preferable to be oblique when considering the fusion with the ultrasonic beam Bb by the vibrator VB, which will be described later. The lens shape of lens section 221B may also be aspherical in shape with the advantage of smooth connection with lens sections 221A and 221C, provided that no disadvantages (e.g., larger side lobes) occur in normal ultrasonic scanning.

In order to accurately capture the position of the puncture needle 3, it is desirable that the positions occupied by the ultrasonic beams Ba, Bb, and Bc transmitted and received by the vibrators VA, VB, and VC are exclusive. This is because exclusivity makes the reflected wave (echo) from the puncture needle 3 easier to distinguish because it is only included in the reflected wave from one of the vibrators VA, VB, or VC.

However, because the directivity of ultrasonic beams has a shape with a gently sloping hem, ultrasonic beams Ba, Bb, Bc overlap at the hem, and thus they are not completely exclusive, as shown in FIG. 4. Thus, there is a way to correct for this by aligning the directivity height of peak of the vibrators VA and VC with the directivity height of vibrators VB in the directivity of ultrasonic beams Ba, Bb, and Bc at a certain depth. If there is a large difference in sensitivity between the vibrators, this will allow for accurate capture of the position of the puncture needle 3. Since there is a difference in sensitivity between vibrators depending on the depth, correction may be made if the difference is large.

The appropriate shape of the acoustic lens 220 in the embodiment is described here. The ultrasonic beam of the vibrator VB becomes narrower from near the vibrator VB toward the focal point. Therefore, the ultrasonic beams by vibrators VA and VC must (be directional to) fill the left and right sides of the ultrasonic beam of vibrator VB becoming thinner. If there is a gap (strictly a zone of low sensitivity of both ultrasonic beams) in the directivity between the ultrasonic beams of vibrator VA and vibrator VB, or between the ultrasonic beams of vibrator VC and vibrator VB, when the puncture needle 3 is located in that area, it becomes difficult to capture. Therefore, it is desirable that the lens of the acoustic lens has such a shape that the ultrasonic beam by vibrator VA and the ultrasonic beam by vibrator VC are deflected inward.

However, when the ultrasonic beams of the vibrators VA and VC converge at a shallow position close to the vibrators VA and VC, in out-of-plane approach puncture, the puncture needle 3 does not enter the ultrasonic beam easily, i.e., it cannot be captured. Considering this, it is desirable that the ultrasonic beams of vibrators VA and VC are deflected, but the converging position is deep or they do not converge.

If an acoustic lens with a lens shape such that the ultrasonic beam by vibrator VA and the ultrasonic beam by vibrator VC are deflected inward, as the depth increases, the ultrasonic beams from vibrators VA and VC overlap with the central ultrasonic beam from vibrator VB, making it impossible to determine the position of the puncture needle 3. Therefore, it is desirable that the deflection angle should not be too large, and the ultrasonic beams of vibrators VA, VB, and VC should be separated so that the needle position can be determined to a depth that does not cause clinical problems.

Though the depth to which they are separated depends on the diagnostic site, for example, when using a high-frequency linear probe as the ultrasound probe 2, it is desirable that separation can be made up to 25 to 30 [mm]. An acoustic lens shape that meets the above requirements is the acoustic lens 220 lens shape with an aspheric shape as shown in FIG. 4. In the acoustic lens 220, the lens section 221B corresponding to the vibrator VB has a tight curvature (curvature radius is small), and the lens section 221A, 221C corresponding to vibrators VA and VC have a loose curvature (curvature radius is large).

In the in-plane approach, the acoustic lens 220 is used as shown in FIG. 4. When switching element SWB is turned on and switching elements SWA and SWC are turned off, ultrasonic waves are transmitted and received using vibrator VB. In this case, the operation is not different from the transmission and reception of ultrasonic waves in conventional ultrasound diagnostic devices, as described above.

If the switching element SWA is turned on and the switching elements SWB and SWC are turned off, ultrasonic waves are transmitted and received by the vibrator VA. Because the lens section 221A corresponding to the vibrator VA has a nearly oblique aspheric shape, the transmitting and receiving beams of ultrasonic waves are deflected toward the center of the vibrator, and the intersection of the transmitting and receiving beams and the centerline is farther away than the focusing point of the lens section 221B corresponding to vibrator VB. When providing curvature in lens sections 221A, 221C, it is desirable to have such a curvature to converge near this intersection. The transmitting and receiving beams of ultrasonic waves formed by the acoustic lens 220 and the vibrators VA, VB, and VC do not overlap or have gaps (sensing blind spots) between them to the desired depth. In the embodiment, in the in-plane approach, tomographic images are formed using respective vibrators VA and VC, in addition to the tomographic image using vibrator VB. Thus, it is possible to capture the puncture needle 3 deviating from the tomographic plane by vibrator VB.

For the out-of-plane approach, as shown in FIG. 5B, in the ultrasound probe 2 of the embodiment, the target T in the subject SU is in the tomographic image by vibrator VB. On the other hand, the puncture needle 3 that has been inserted can be captured much earlier on the tomographic image by vibrator VA (or vibrator VC) than the case of using a general ultrasound probe. As an example, in a case where a target with a 45 degree angle of penetration and a depth of 1 cm is penetrated, when the ultrasonic beam width of vibrator VB is 1.8 mm, the puncture needle was first seen about 1 mm in front of the target with a general ultrasound probe, whereas confirmation of puncture needle was possible from approximately 4 mm in front of the target with the ultrasound probe 2 in the embodiment. Thus, when the out-of-plane approach of the embodiment is used, the position of puncture needle 3 can be confirmed well in front of the target T, facilitating the puncture operation.

Referring now to FIG. 3, the transmission/reception sequence of ultrasonic waves of the vibrators 210 for the generation of B-mode image data in B-mode or color Doppler mode of the embodiment is described. As described above, in the configuration using the acoustic lens 220, the vibrators VA, VB, VC, and the switching elements SWA, SWB, SWC, ultrasonic waves are transmitted and received using vibrators VA and VC to obtain the reflected waves (echoes) of the puncture needle 3 deviating from the ultrasonic beam Bb formed by the vibrator VB. In this case, scanning (ultrasonic wave transmission and reception) can be performed in the order of, for example, vibrators V1a, V1b, V1c, V2a, V2b, V2c, V3a, V3b, V3c . . . The setting information for such scanning sequences is stored in the short axis aperture controller 18.

In this case, however, the frame rate of the B-mode tomographic image display is reduced to one-third because the number of transmissions and receptions is tripled. Therefore, the scanning of vibrators VA and VC for the capture of the puncture needle 3 can be thinned out, e.g., vibrators V1a, V1b, V1c, V2b, V3a, V3b, V3c, V4b, V5a, V5b, V5c . . . in this order to reduce frame rate reduction. The above explanation describes the case where one vibrator is used for scanning in the long axis direction for the sake of simplicity, but in reality, multiple vibrators are used for transmitting and receiving beam formation in the long axis direction. In addition, it is also possible to increase the frame rate by using parallel reception in the long axis direction, which is already well known.

The above description is the transmission/reception sequence for B-mode image data generation in B-mode or color Doppler mode. The transmission/reception sequence for color flow image data generation in color Doppler mode is such that ultrasonic waves are transmitted and received multiple times (repetition number is n) at the same position in one frame at each vibrator corresponding to the ROI among the vibrators 210.

In the above description of the ultrasound probe 2, the case in which the puncture needle 3 is viewed as the recognition object is explained, but the same applies to the case in which tissue such as the subject's tumor is viewed as the recognition object.

Figure 7A:
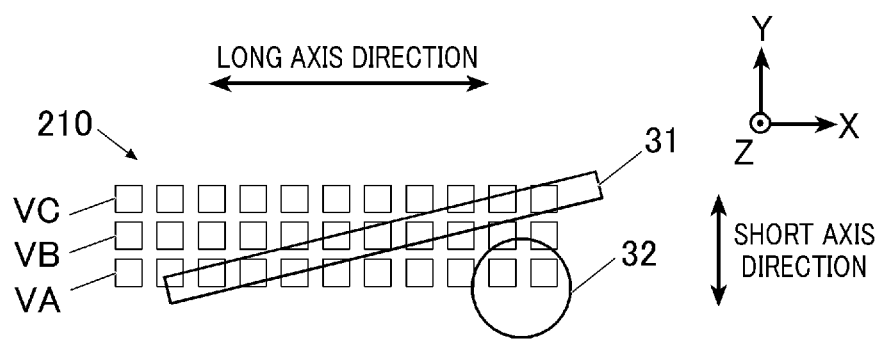
FIG. 7A is a plan view showing vibrators of the ultrasound probe and reflectors in the first three-dimensional image generation method.
Figure 7B:
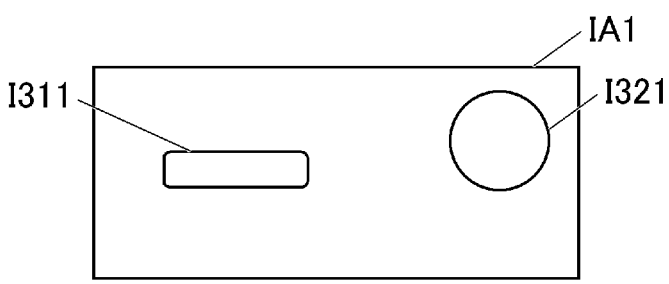
FIG. 7B is a view showing a B-mode image corresponding to a first vibrator.
Figure 7C:
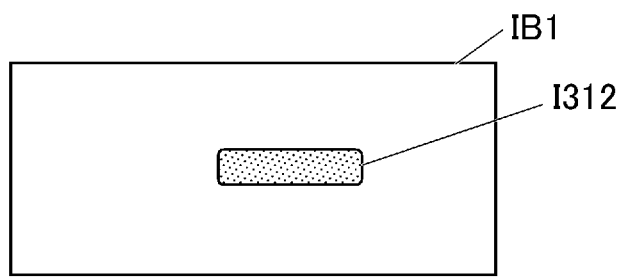
FIG. 7C is a view showing a B-mode image corresponding to a second vibrator.
Figure 7D:
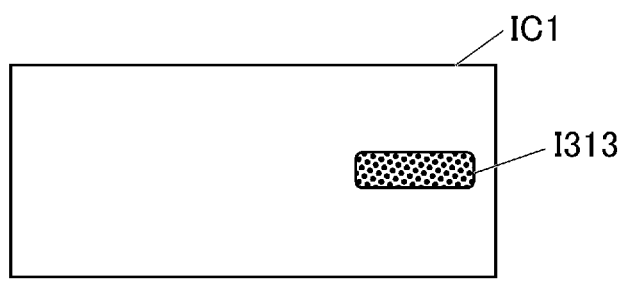
FIG. 7D is a view showing a B-mode image corresponding to a third vibrator.
Figure 7E:
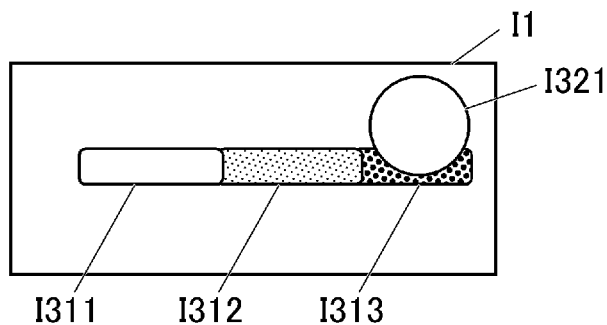
FIG. 7E is a view showing a three-dimensional image in the B-mode.

The operation of the ultrasound diagnostic device 100 is described next with reference to FIG. 6 through FIG. 14C. FIG. 6 is a flowchart showing the first three-dimensional image display processing. FIG. 7A is a plan view showing vibrators VA. VB. VC of the ultrasound probe 2 and reflectors 31, 32 in the first three-dimensional image generation method. FIG. 7B is a view showing a B-mode image IA1 corresponding to vibrator VA. FIG. 7C is a view showing B-mode image D31 corresponding to vibrator VB. FIG. 7D is a view showing B-mode image IC1 corresponding to vibrator VC. FIG. 7E is a view showing a three-dimensional image I1 in the B-mode.

Figure 8A:
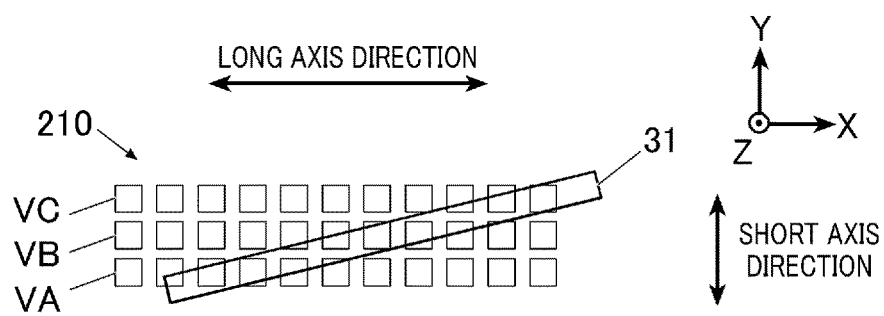
FIG. 8A is a plan view showing vibrators of the ultrasound probe and a reflector in the second three-dimensional image generation method.
Figure 8B:
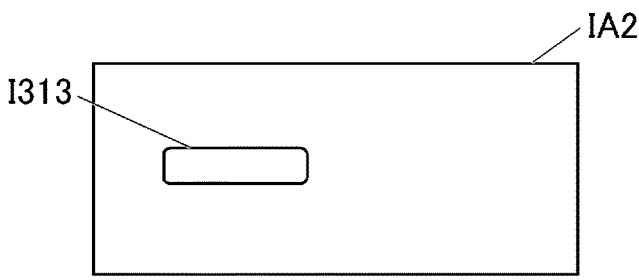
FIG. 8B is a view showing a B-mode image corresponding to the first vibrator.
Figure 8C:
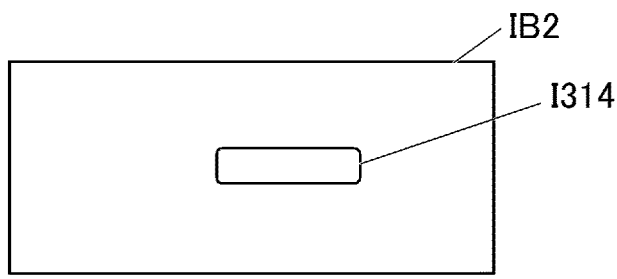
FIG. 8C is a view showing a B-mode image corresponding to the second vibrator.
Figure 8D:
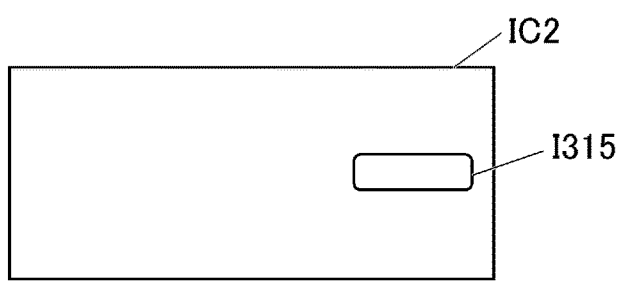
FIG. 8D is a view showing a B-mode image corresponding to the third vibrator.
Figure 8E:
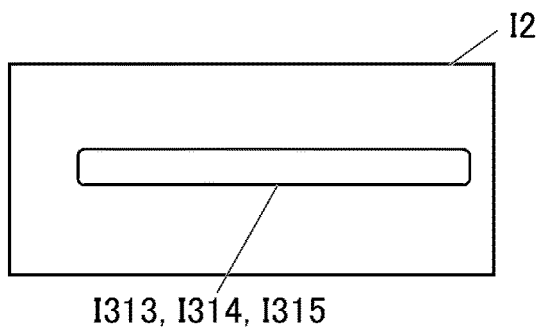
FIG. 8E is a view showing a three-dimensional image in the B-mode.
Figure 9A:
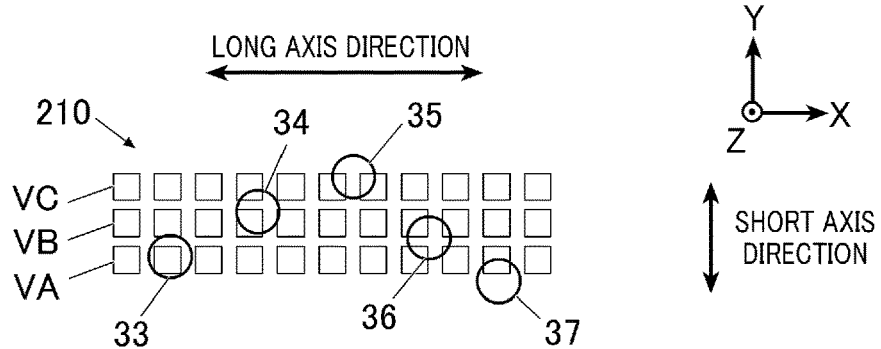
FIG. 9A is a plan view showing vibrators of the ultrasound probe and reflectors in the third three-dimensional image generation method.
Figure 9B:
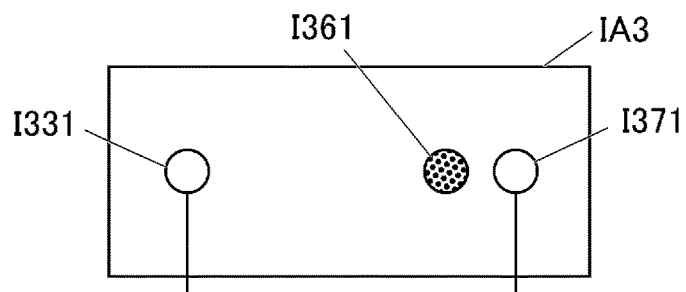
FIG. 9B is a view showing a B-mode image corresponding to the first vibrator.
Figure 9C:
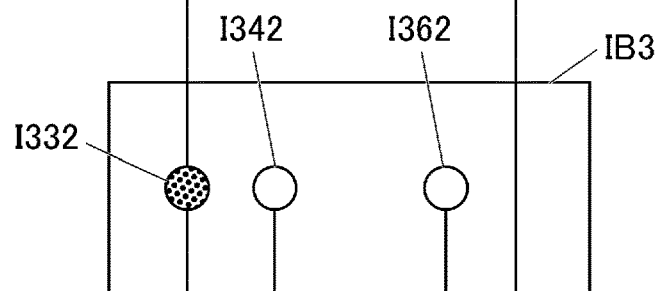
FIG. 9C is a view showing a B-mode image corresponding to the second vibrator.
Figure 9D:
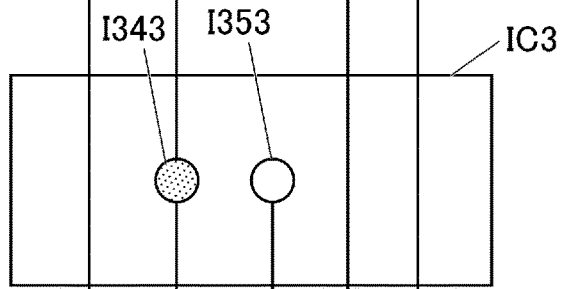
FIG. 9D is a view showing a B-mode image corresponding to the third vibrator.
Figure 9E:
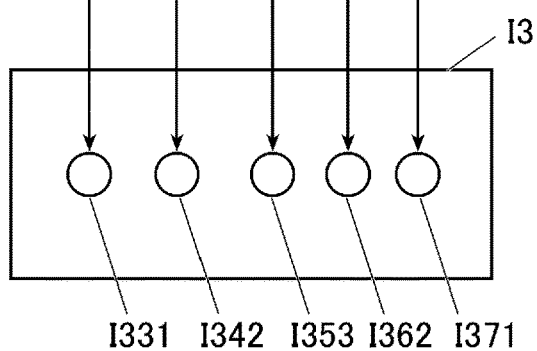
FIG. 9E is a view showing a three-dimensional image in the B-mode.
Figure 10A:
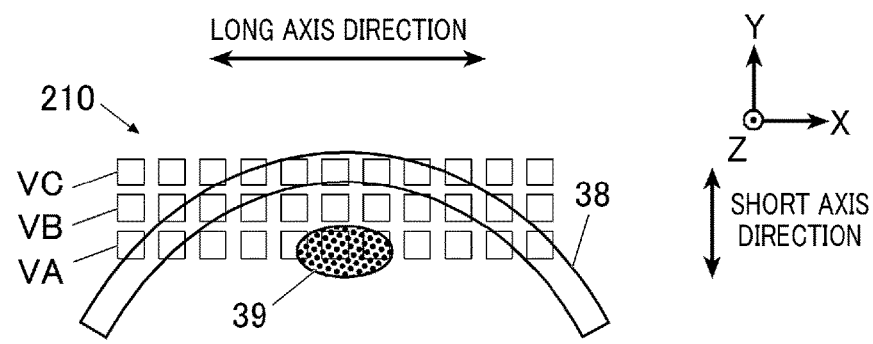
FIG. 10A is a plan view showing vibrators of the ultrasound probe and reflectors in the fourth three-dimensional image generation method.
Figure 10B:
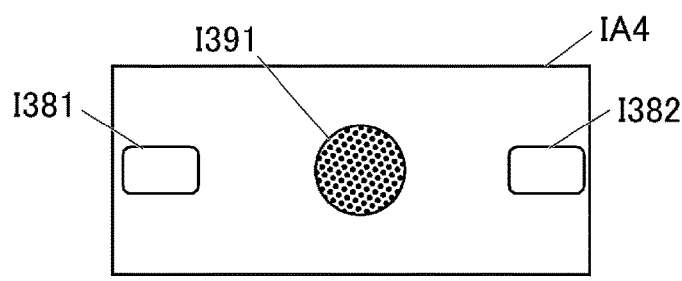
FIG. 10B is a view showing a B-mode image corresponding to the first vibrator.
Figure 10C:
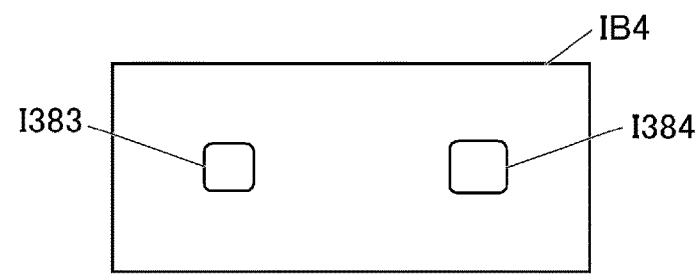
FIG. 10C is a view showing a B-mode image corresponding to the second vibrator.
Figure 10D:
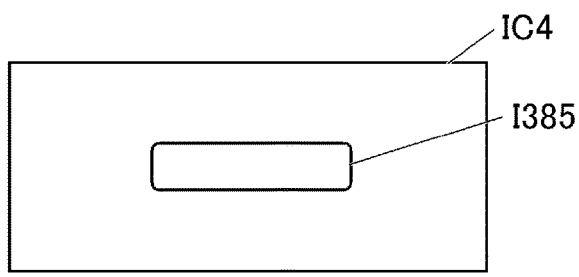
FIG. 10D is a view showing a B-mode image corresponding to the third vibrator.
Figure 10E:
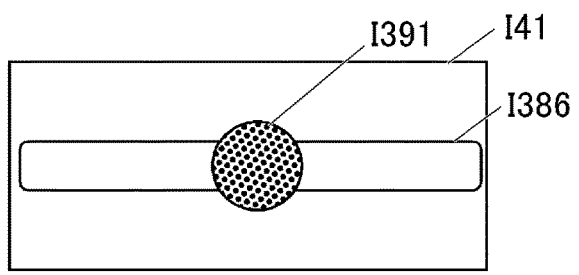
FIG. 10E is a view showing a three-dimensional image in the B-mode.
Figure 10F:
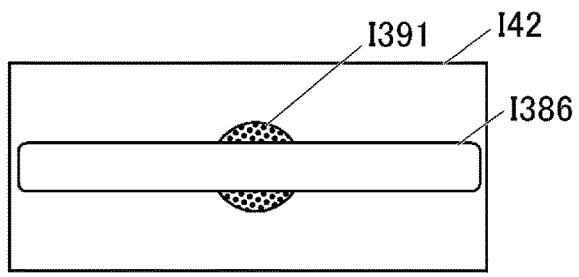
FIG. 10F is a view showing a three-dimensional image in the B-mode.

FIG. 8A is a plan view showing vibrators VA, VB, VC of the ultrasound probe 2 and a reflector 31 in the second three-dimensional image generation method. FIG. 8B is a view showing B-mode image IA2 corresponding to vibrator VA. FIG. 8C is a view showing B-mode image IB2 corresponding to vibrator VB. FIG. 8D is a view showing B-mode image IC2 corresponding to vibrator VC. FIG. 8E is a view showing a three-dimensional image I2 in the B-mode. FIG. 9A is a plan view showing vibrators VA, VB, VC of the ultrasound probe 2 and reflectors 33, 34, 35, 36, 37 in the third three-dimensional image generation method. FIG. 9B is a view showing B-mode image IA3 corresponding to vibrator VA. FIG. 9C is a view showing B-mode image IB3 corresponding to vibrator VB. FIG. 9D is a view showing B-mode image IC3 corresponding to vibrator VC. FIG. 9E is a view showing a three-dimensional image I3 in the B-mode. FIG. 10A is a plan view showing vibrators VA, VB, VC of the ultrasound probe 2 and reflectors 38, 39 in the fourth three-dimensional image generation method. FIG. 10B is a view showing B-mode image IA4 corresponding to vibrator VA. FIG. 10C is a view showing B-mode image IB4 corresponding to vibrator VB. FIG. 10D is a view showing B-mode image IC4 corresponding to vibrator VC. FIG. 10E is a view showing a three-dimensional image I41 in the B-mode. FIG. 10F is a view showing a three-dimensional image I42 in the B-mode.

Figure 11A:
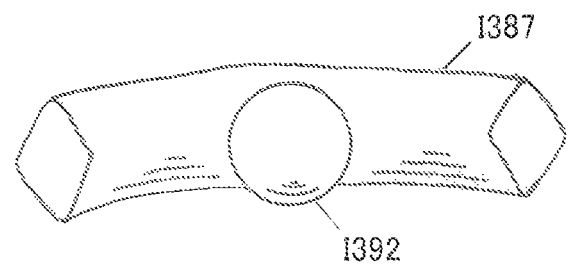
FIG. 11A is a view showing a three-dimensional image in the fifth three-dimensional image generation method.
Figure 11B:
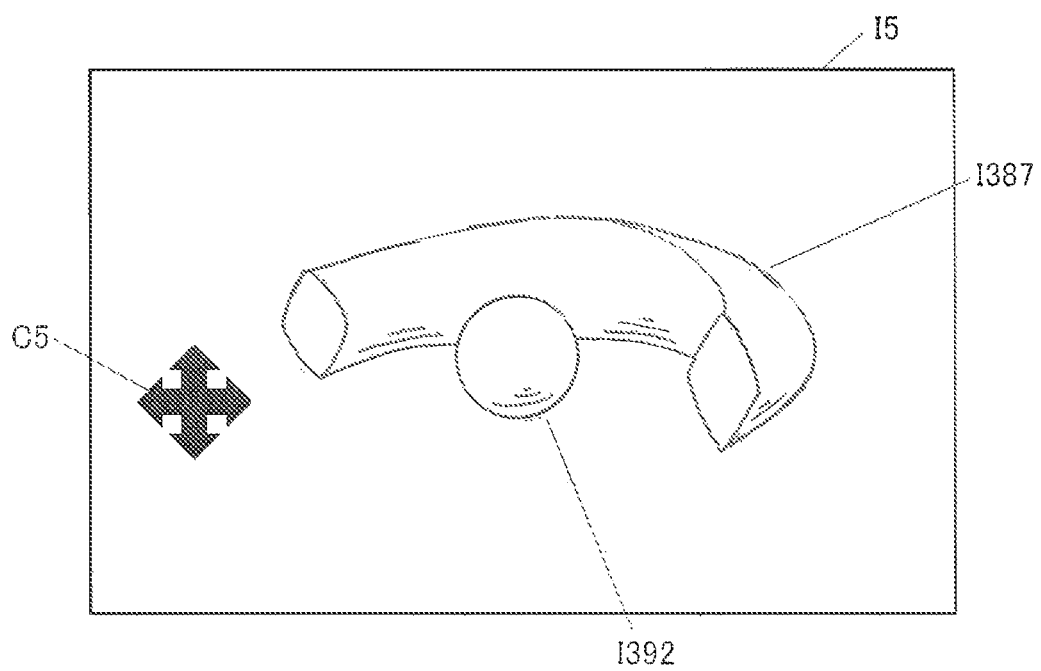
FIG. 11B is a view showing a display screen having a three-dimensional image.
Figure 12A:
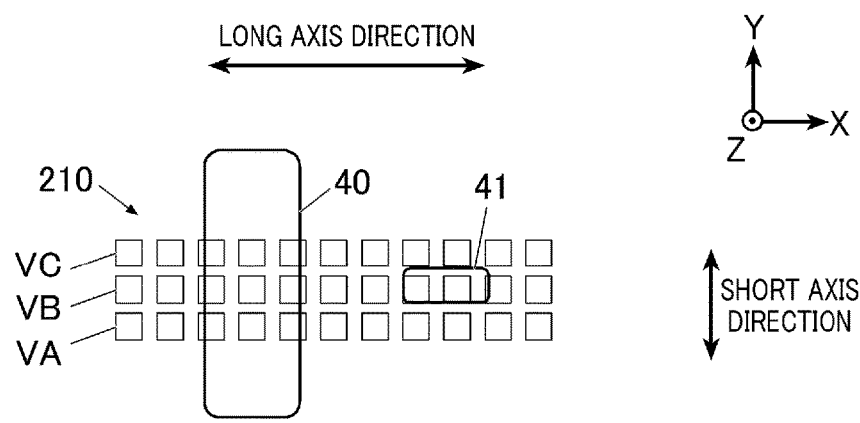
FIG. 12A is a plan view showing vibrators of the ultrasound probe and reflectors in the sixth three-dimensional image generation method.
Figure 12B:
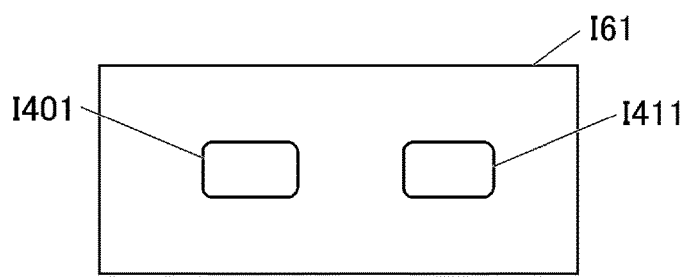
FIG. 12B is a view showing a three-dimensional image in the B-mode.
Figure 12C:
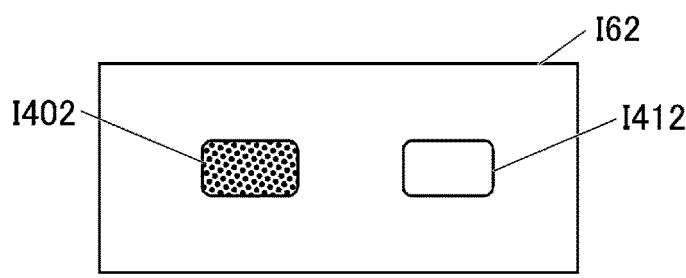
FIG. 12C is a view showing a three-dimensional image in the B-mode.
Figure 13A:
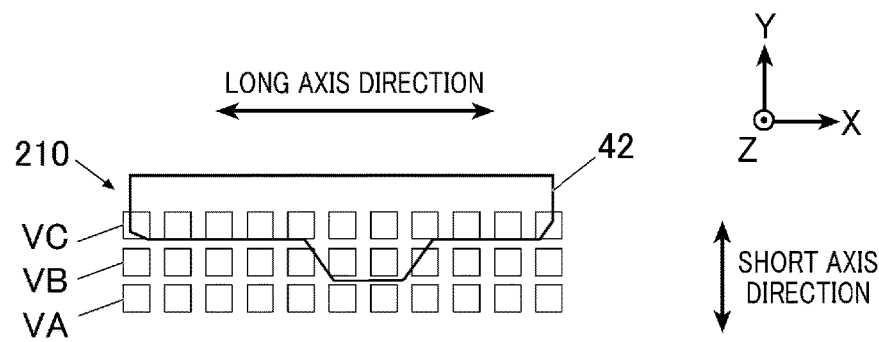
FIG. 13A is a plan view showing vibrators of the ultrasound probe and a reflector in the seventh three-dimensional image generation method.
Figure 13B:
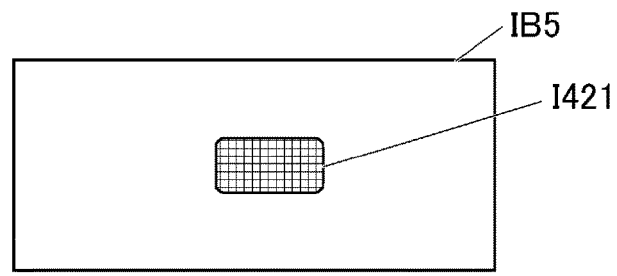
FIG. 13B is a view showing a B-mode image corresponding to the second vibrator.
Figure 13C:
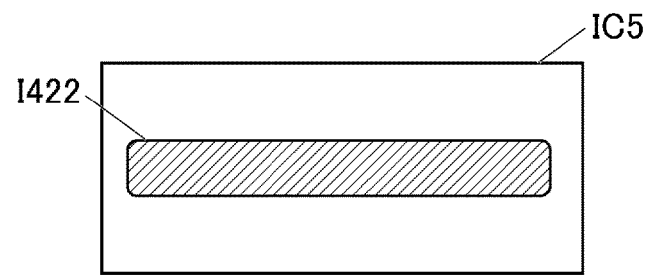
FIG. 13C is a view showing a B-mode image corresponding to the third vibrator.
Figure 13D:
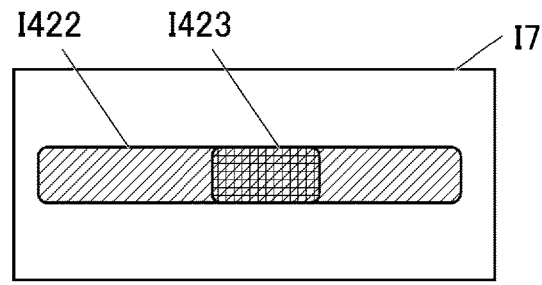
FIG. 13D is a view showing a three-dimensional image in the B-mode.

FIG. 11A is a view showing three-dimensional images I387, I392 in the fifth three-dimensional image generation method. FIG. 11B is a view showing a display screen I5 having three-dimensional images I387, I392. FIG. 12A is a plan view showing vibrators VA, VB, VC of the ultrasound probe 2 and reflectors 40, 41 in the sixth three-dimensional image generation method. FIG. 12B is a view showing three-dimensional image I61 in the B-mode. FIG. 12C is a view showing three-dimensional image I62 in the B-mode. FIG. 13A is a plan view showing vibrators VA, VB, VC of the ultrasound probe 2 and reflector 42 in the seventh three-dimensional image generation method. FIG. 13B is a view showing B-mode image I35 corresponding to vibrator VB. FIG. 13C is a view showing B-mode image IC5 corresponding to vibrator VC. FIG. 13D is a view showing three-dimensional image I7 in the B-mode.

Figure 14A:
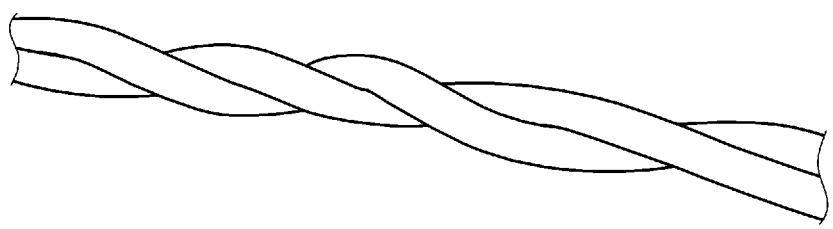
FIG. 14A is a view showing a silicon tube as a subject.
Figure 14B:
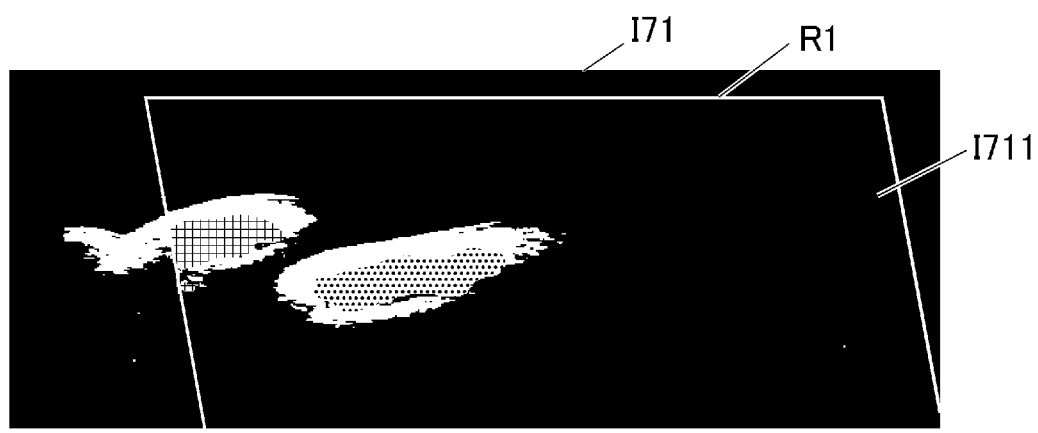
FIG. 14B is a view showing a composite image including a color flow image of ROI.
Figure 14C:
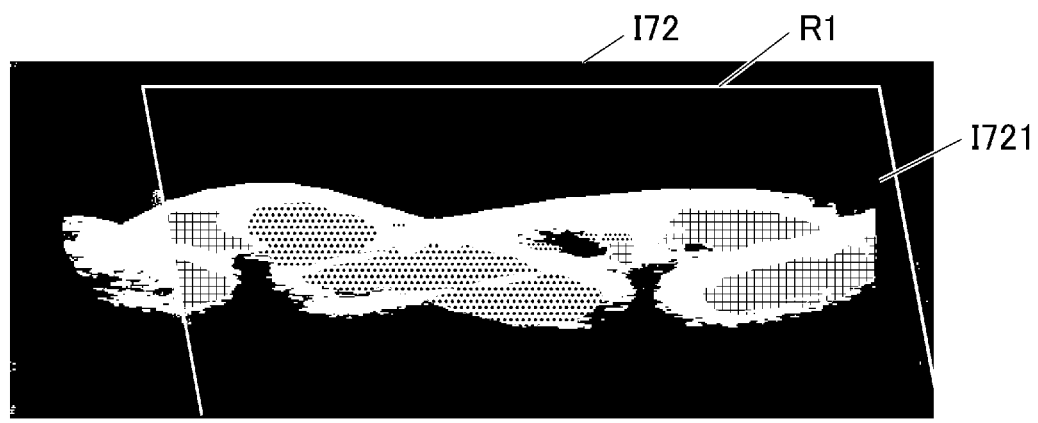
FIG. 14C is a view showing a composite image including a three-dimensional image of a color flow image of ROI.

FIG. 14A is a view showing a silicon tube as a subject. FIG. 14B is a view showing a composite image I71 including a color flow image of ROI R1. FIG. 14C is a view showing a composite image I72 including a three-dimensional image of a color flow image of ROI R1.

Referring to FIGS. 6 through 7E, the first three-dimensional image display processing performed by the ultrasound diagnostic device 100 is described. The first three-dimensional image display processing is the live display of a B-mode three-dimensional image of the subject for the operator to confirm the puncture needle 3 in the subject as the recognition object, the tissue of the subject, etc. As the three-dimensional image generation method of the first three-dimensional image display processing, the description is made for an example using the first three-dimensional image generation method of generating three-dimensional image data by increasing the brightness of B-mode image closer to the viewpoint position of an operator such as a physician among B-mode images corresponding to the respective vibrators VA, VB, and VC of the ultrasound probe 2.

In advance, for example, an operator such as a physician waits in the examination room where the ultrasound diagnostic device 100 is installed, and the patient as the subject enters the examination room and lies on the bed. Then, in the ultrasound diagnostic device 100, for example, in response to a trigger that various setting information such as frame rate of the first three-dimensional image display processing and the instruction to execute the first three-dimensional image display processing are received from the operator via the operation input interface 17, the controller 11 executes the first three-dimensional image display processing according to the first three-dimensional image display program stored in the HDD.

First, the controller 11 accepts input of the viewpoint position of the three-dimensional image from the operator via the operation input interface 17 (step S11). In step S11, for example, one of the viewpoint position on the vibrator VA side (−Y side) of FIG. 3 and the viewpoint position on the vibrator VC side (+Y side) is selected and input.

The controller 11 causes the transmitter 12 to start generating drive signals in response to the input various setting information, inputs the drive signal to each vibrator of the vibrators VA, VB, and VC of the ultrasound probe 2 to emit transmission ultrasonic waves and receive reflected ultrasonic waves (echoes) by switching of the switching element 230 according to the setting information of transmission/reception sequence stored in the short axis aperture controller 18 via the short axis aperture controller 18 and causes the receiver 13 to generate a received signal (step S12). The received signals obtained in step S12 are acquired for each frame at the same time corresponding to each vibrator VA, VB, VC in order according to the transmission/reception sequence.

The controller 11 causes the image generator 14 to generate one frame of B-mode image data from the received signal corresponding to the vibrator VA generated by the receiver 13 in step S12 (step S13). The controller 11 adjusts the pixel brightness (brightness value) according to the distance to the present B-mode image data (ultrasonic beam Ba) from the viewpoint position input in step S11 in the B-mode image data generated in step S13 by the three-dimensional image generator 15 according to the input various setting information (step S14). In step S14, and steps S16 and S18 below, for example, the brightness of the pixel in the B-mode image data corresponding to each of the vibrators VA, VB, and VC is adjusted such that, for pixels of the same brightness, the one closest to the viewpoint position has the highest brightness, and the further away the pixel is, the lower the brightness, as for the B-mode image data corresponding to vibrator VA in step S13, the B-mode image data corresponding to vibrator VB in step S15 described below, and the B-mode image data corresponding to vibrator VA in step S17 described below.

The controller 11 causes the image generator 14 to generate one frame of B-mode image data from the received signal corresponding to the vibrator VB generated by the receiver 13 in step S12 according to the various setting information input (step S15). The controller 11 adjusts the pixel brightness according to the distance to the present B-mode image data (ultrasonic beam Bb) from the viewpoint position input in step S11 in the B-mode image data generated in step S15 by the three-dimensional image generator 15 according to the input various setting information (step S16).

The controller 11 causes the image generator 14 to generate one frame of B-mode image data from the received signal corresponding to the vibrator VC generated by the receiver 13 in step S12 according to the various setting information input (step S17). The controller 11 adjusts the pixel brightness according to the distance to the present B-mode image data (ultrasonic beam Bc) from the viewpoint position input in step S11 in the B-mode image data generated in step S17 by the three-dimensional image generator 15 according to the input various setting information (step S18).

The controller 11 causes the three-dimensional image generator 15 to combine (add) the three B-mode image data of frames at the same time whose brightness was adjusted in steps S14, S16, and S18 to generate the three-dimensional B-mode image data of one frame (step S19). Then, the controller 11 displays the B-mode three-dimensional image data generated in step S19 by the three-dimensional image generator 15 as a three-dimensional image on the display 16 (step S20).

The controller 11 determines whether or not an instruction to change the viewpoint position of the three-dimensional image has been input by the operator via the operation input interface 17 (step S21). If the instruction to change the viewpoint position of the three-dimensional image has been input (step S21; YES), the processing proceeds to step S11. If the instruction to change the viewpoint position of the three-dimensional image has not been input (step S21; NO), the controller 11 determines whether or not to end the first three-dimensional image display processing depending on whether an instruction to end the first three-dimensional image display processing has been input from the operator via the operation input interface 17 (step S22).

If the first three-dimensional image display processing is not to be ended (step S22; NO), the processing proceeds to step S12. If the first three-dimensional image display processing is to be ended (step S22; YES), the controller 11 ends the first three-dimensional image display processing.

Description is made for a specific example of the first three-dimensional image generation method of the first three-dimensional image display processing with reference to FIG. 7A through FIG. 7E. As shown in FIG. 7A, there is considered a case where, when looking at the ultrasound probe 2 in FIG. 3 from the +Z direction, cylindrical reflector 31 and spherical reflector 32 are located as recognition objects, in the subject below the vibrators 210 (on the −Z direction side), and reflectors 31, 32 are observed. Reflectors 31 and 32 are, for example, the subject's tissue, which is assumed to have uniform brightness when made into a B-mode image. It is assumed that, in step S11 of the first three-dimensional image display processing, the viewpoint position on the vibrator VA side (−Y side) of the vibrator 210 was input.

As shown in FIG. 7B, B-mode image data for B-mode image IA1 is generated in step S13. B-mode image IA1 includes reflector image I311 of reflector 31 and reflector image I321 of reflector 32. In step S14, the vibrator VA (ultrasonic beam Ba) is located closest to the viewpoint position, and thus, the brightness of reflector images I311, I321 is adjusted to be highest. Before brightness adjustment, the brightness of reflector images I311, I321 is same as the brightness of reflector images I312, I313 described later.

As shown in FIG. 7C, B-mode image data for B-mode image IB1 is generated in step S15. B-mode image IB1 includes reflector image I312 of reflector 31. In step S16, the vibrator VB (ultrasonic beam Bb) is the second closest to the viewpoint position, and thus, the brightness of reflector images I312 is adjusted to be the second highest.

As shown in FIG. 7D, B-mode image data for B-mode image IC1 is generated in step S17. B-mode image IC1 includes reflector image I313 of reflector 31. In step S18, the vibrator VC (ultrasonic beam Bc) is furthest from the viewpoint position, and thus, the brightness of reflector images I313 is adjusted to be the third highest (to be the lowest).

As shown in FIG. 7E, in step S19, the B-mode image data of B-mode image IA1, the B-mode image data of B-mode image IB1 and the B-mode image data of B-mode image IC1 are combined (added) to generate three-dimensional image data of the three-dimensional image I1 as the pseudo three-dimensional image in B-mode. The three-dimensional image I1 in B-mode includes (the unified image of) reflector images I311, I312, and I313 and reflector image I321. In step S20, the three-dimensional image I1 in B-mode is displayed on the display 16. This allows the operator to know the positional relationship of the two reflectors 31, 32 in the short axis direction by observing the brightness of the three-dimensional image I1 of B-mode.

Description is made for a specific example of the second three-dimensional image generation method of the first three-dimensional image display processing with reference to FIG. 8A through FIG. 8E. Here, description is made for an example using the second three-dimensional image generation method of generating the three dimensional image data by adding, without change, the B-mode images respectively corresponding to the vibrators VA, VB, VC of the ultrasound probe 2, as the three-dimensional image generation method of the first three-dimensional image display processing.

The second three-dimensional image generation method also uses the ultrasound diagnostic device 100 to perform similar processing to the first three-dimensional image display processing in FIG. 6, but steps S11, S14, S16, S18, and S21 are assumed not to be performed.

As shown in FIG. 8A, there is considered a case where, when looking at the ultrasound probe 2 in FIG. 3 from the +Z direction, cylindrical reflector 31 is located as the recognition object, in the subject below the vibrators 210 (on the −Z direction side), and the reflector 31 is observed.

As shown in FIG. 8B, B-mode image data for B-mode image IA2 is generated in step S13 of the first three-dimensional image display processing. B-mode image IA2 includes reflector image I313 of reflector 31. The brightness of reflector images I313 is same as the brightness of reflector images I314, I315 described later.

As shown in FIG. 8C, B-mode image data for B-mode image IB2 is generated in step S15. B-mode image IB2 includes reflector image I314 of reflector 31. As shown in FIG. 8D, B-mode image data for B-mode image IC2 is generated in step S17. B-mode image IC2 includes reflector image I315 of reflector 31.

As shown in FIG. 8E, in step S19, the B-mode image data for B-mode image IA2, the B-mode image data of B-mode image IB2 and the B-mode image data of B-mode image IC2 are combined (added) to generate three-dimensional image data of the three-dimensional image I2 as the pseudo three-dimensional image in B-mode. The three-dimensional image I2 in B-mode includes (the unified image of) reflector images I313, I314, and I315. In step S20, the three-dimensional image I2 in B-mode is displayed on the display 16. This allows the overall image of the reflector 31 (the unified image of reflector images I313, I314, and I315) to be depicted, and the operator can get an overall image of the short axis direction of the reflector 31 by observing the three-dimensional image I2 in B-mode. The operator can easily grasp the shape of the organ as a reflector in the subject, for example.

Description is made for a specific example of the third three-dimensional image generation method of the first three-dimensional image display processing with reference to FIG. 9A through FIG. 9E. Here, description is made for an example using the third three-dimensional image generation method of generating the three-dimensional image data by selecting the pixel of maximum brightness among the pixels at the same position of the B-mode images respectively corresponding to the vibrators VA, VB, VC of the ultrasound probe 2, as the three-dimensional image generation method of the first three-dimensional image display processing.

The third three-dimensional image generation method also uses the ultrasound diagnostic device 100 to perform similar processing to the first three-dimensional image display processing in FIG. 6, but steps S11 and S21 are assumed not to be performed.

As shown in FIG. 9A, there is considered a case where, when looking at the ultrasound probe 2 in FIG. 3 from the +Z direction, spherical reflectors 33, 34, 35, 36, 37 are located as recognition objects in the subject below the vibrators 210 (on the −Z direction side), and reflectors 33, 34, 35, 36, 37 distributed in the short axis direction are observed.

As shown in FIG. 9B, B-mode image data for B-mode image IA3 is generated in step S13 of the first three-dimensional image display processing. B-mode image IA3 includes reflector image I331 of reflector 33, reflector image I361 of reflector 36, and reflector image I371 of reflector 37. The reflector images I331 has the same size and shape as and different brightness from the reflector image I332 described later. The reflector image I342 and reflector image I343 described later have the same size and shape and different brightness. The reflector image I361 and reflector image I362 described later have the same size and shape and different brightness.

As shown in FIG. 9C, B-mode image data for B-mode image IB3 is generated in step S15. B-mode image IB3 includes reflector image I332 of reflector 33, reflector image I342 of reflector 34, and reflector image I362 of reflector 36. As shown in FIG. 9D, B-mode image data for B-mode image IC3 is generated in step S17. B-mode image IC3 includes reflector image I343 of reflector 34 and reflector image I353 of reflector 35.

In step S14, the brightness of the pixel with the highest brightness in B-mode image IA3 is selected among pixels with a reflector image at the same position in B-mode images IA3, IB3 and IC3. In step S16, the brightness of the pixel with the highest brightness in B-mode image IB3 is selected among pixels with a reflector image at the same position in B-mode images IA3, IB3 and IC3. In step S18, the brightness of the pixel with the highest brightness in B-mode image IC3 is selected among pixels with a reflector image at the same position in B-mode images IA3, IB3 and IC3.

As shown in FIG. 9E, in step S19, B-mode image data in which the pixel with the highest brightness in B-mode image IA3 is selected, B-mode image data in which the pixel with the highest brightness (maximum brightness) in B-mode image IB3 is selected, and B-mode image data in which the pixel with the highest brightness in B-mode image IC3 is selected are combined (added) to generate three-dimensional image data of the three-dimensional image I3 as the pseudo three-dimensional image in B-mode. The three-dimensional image I3 in B-mode includes reflector images I331, I342, I353, I362 and I371. In step S20, the three-dimensional image I3 in B-mode is displayed on the display 16. Thus, it is possible to clearly depict the reflector which has the brightness being partially high in the short axis direction since the width is large in the short axis direction and the ultrasound image data is obtained by the ultrasonic beam of each of the vibrators VA, VB, VC.

Description is made for a specific example of the fourth three-dimensional image generation method of the first three-dimensional image display processing with reference to FIG. 10A through FIG. 10F. Here, description is made for an example using, as the three-dimensional image generation method of the first three-dimensional image display processing, the fourth three-dimensional image generation method of generating the three-dimensional image data by selecting the pixel of B-mode image on which superimposing is to be performed in response to each brightness difference between pixels exceeding a predetermined threshold value which was set in advance in the B-mode image on which superimposing is to be performed and the B-mode image to be superimposed when, on the B-mode image furthest from the viewpoint position, the B-mode images closer than the furthest B-mode image is superimposed in the descending order of distance from the viewpoint position among the B-mode images corresponding to the vibrators VA, VB, VC of the ultrasound probe 2.

The fourth three-dimensional image generation method also uses the ultrasound diagnostic device 100 to perform similar processing to the first three-dimensional image display processing in FIG. 6.

As shown in FIG. 10A, there is considered a case where, when looking at the ultrasound probe 2 in FIG. 3 from the +Z direction, reflector 38 which is cylindrical with an arc shape in the axial direction viewed from the top (+Z direction), and reflector 39 which is nearly oblong spherical are located as recognition objects in the subject below the vibrators 210 (on the −Z direction side), and reflectors 38, 39 are observed. It is assumed that the viewpoint position on the vibrator VA side (−Y side) of the vibrators 210 was input in step S11 of the first three-dimensional image display processing.

As shown in FIG. 10B, B-mode image data for B-mode image IA4 is generated in step S13. B-mode image IA4 includes reflector images I381, I382 of reflector 38, and reflector image I391 of reflector 39. The reflector images I381, I382 have the same brightness as the reflector images I383, I384, I385 described later. The reflector images I381, I382, I383, I384, I385 have different brightness from that of reflector image I391.

As shown in FIG. 10C, B-mode image data for B-mode image IB4 is generated in step S15. B-mode image IB4 includes reflector images I383, I384 of reflector 38. As shown in FIG. 10D, B-mode image data for B-mode image IC4 is generated in step S17. B-mode image IC4 includes reflector image I385 of reflector 38.

In step S14, if the brightness difference between B-mode images IA4 and IB4 exceeds a predetermined threshold value set in advance for each pixel having a reflector image at the same position in B-mode images IA4, IB4, the brightness of the pixel in B-mode image IA4 on the most viewpoint position side is not selected. In step S16, for each pixel that has a reflector image at the same position in B-mode images IA4, IB4, and IC4, if the brightness difference between B-mode images IA4 and IB4 exceeds a predetermined threshold value, the brightness of the pixel in B-mode image IB4 on the opposite side of the viewpoint position (the side on which superimposing is to be performed) is selected. If the brightness difference between B-mode images IB4 and IC4 exceeds a predetermined threshold value, the brightness of the pixel in B-mode image IB4 on the viewpoint position side is not selected. In step S18, for each pixel that has a reflector image at the same position in B-mode images IB4, IC4, if the brightness difference between B-mode images IA4 and IC4 exceeds a predetermined threshold value, the brightness of the pixel in B-mode image IC4 on the most opposite side of the viewpoint position (the side on which superimposing is to be performed) is selected.

As shown in FIG. 10F, in step S19, the B-mode image data in which the brightness of pixel in B-mode image IA4 is selected, B-mode image data in which the brightness of pixel in B-mode image IB4 is selected, and B-mode image data in which the brightness of pixel in B-mode image IC4 is selected are combined (added), to generate three-dimensional image data for B-mode three-dimensional image I42.

As shown in FIG. 10E, if the B-mode image data of B-mode image IA4, the B-mode image data of B-mode image IB4, and the B-mode image data of B-mode image IC4 are combined (added) in order from the opposite side to the viewpoint position toward the viewpoint position side, then three-dimensional image data for B-mode three-dimensional image I41 is generated. Three-dimensional image I41 is correct for stereoscopic viewing, but is undesirable when observing an arc-shaped reflector 38. In contrast, three-dimensional image I42 can be useful when observing an arc-shaped reflector 38.

Description is made for a specific example of the fifth three-dimensional image generation method of the first three-dimensional image display processing with reference to FIG. 11A and FIG. 11B. Here, description is made for an example using the fifth three-dimensional image generation method of generating the three-dimensional image data of an image with a three-dimensionality (three-dimensionalized image) from each B-mode image corresponding to the vibrators VA, VB, and VC of the ultrasound probe 2, as the three-dimensional image generation method of the first three-dimensional image display processing.

The fifth three-dimensional image generation method also uses the ultrasound diagnostic device 100 to perform similar processing to the first three-dimensional image display processing in FIG. 6, but steps S14, S16 and S18 are assumed not to be performed.

Here, description is made for a case of observing arc-shaped reflector 38 and nearly spherical reflector 39 as in FIG. 10A and FIG. 10B of the description of the fourth three-dimensional image generation method. First, in step S11 of the first three-dimensional image display processing, flexible input of a three-dimensional viewpoint position with a changeable viewing angle is accepted from the operator via the mouse, trackball, etc. of the operation input interface 17. In step S11, for example, cursor C5 shown in FIG. 11B is displayed on the display 16 and operation input for changing the three-dimensional viewpoint position to the displayed cursor C5 is accepted.

In step S19, from the B-mode image data of vibrators VA, VB, and VC obtained in steps S13, S15, and S17, three-dimensional image data of the three-dimensionalized image corresponding to the viewpoint position (and viewing angle) input in step S11 is generated. For example, from the B-mode image data for B-mode image IA4 in FIG. 10B, B-mode image data for B-mode image IB4 in FIG. 10C, B-mode image data for B-mode image IC4 in FIG. 10D, the interpolation is done appropriately, and three-dimensional image data as a three-dimensionalized image with three-dimensional image I387 of reflector 38 and three-dimensional image I392 of reflector 39 shown in FIG. 11A is generated.

In step S20, three-dimensional image data of three-dimensional images I387, I392 of the three-dimensionalized image of reflectors 38, 39 generated in step S19 and the display screen 15 including the cursor C5 are displayed on the display 16. Three-dimensional images I387 and I392 shown in FIG. 11A have a different viewpoint position from that of three-dimensional images I387 and I392 shown in FIG. 11B. For example, when displaying a display screen including the three-dimensional images I387 and I39 shown in FIG. 11A, the input to change the viewpoint position in step S21 and S11 is made and the display screen I5 containing three-dimensional images I387, I392 shown in FIG. 11B is displayed. For example, cursor C5 is at the three-dimensional viewpoint position and operation input for changing the three-dimensional viewpoint position is made to three-dimensionally move the cursor C5 position with respect to the three-dimensional images I387, I392. As shown in FIG. 11A and FIG. 11B, three-dimensional images I387, I392 may be displayed as a monochrome display with intermediate color of gray, and color display may be performed with yellow, green, and blue in this order, corresponding to light gray, gray, and dark gray in this order.

The display screen I5 allows the viewer to change the viewpoint position (and viewing angle) to observe the subject, and to see more clearly the positional relationship of the recognition objects (reflectors 38, 39) within the subject.

Description is made for a specific example of the sixth three-dimensional image generation method of the first three-dimensional image display processing with reference to FIG. 12A through FIG. 12C. Here, description is made for an example using the sixth three-dimensional image generation method of generating the three-dimensional image data of three-dimensional image as pseudo three-dimensional image to highlight the changes in the short axis direction from the B-mode images corresponding to the vibrators VA, VB, and VC of the ultrasound probe 2, as the three-dimensional image generation method of the first three-dimensional image display processing.

The sixth three-dimensional image generation method also uses the ultrasound diagnostic device 100 to perform similar processing to the first three-dimensional image display processing in FIG. 6, but steps S11, S14, S16, S18 and S21 are assumed not to be performed.

As shown in FIG. 12A, there is considered a case where, when looking at the ultrasound probe 2 in FIG. 3 from the +Z direction, nearly cuboid reflectors 40, 41 are located as recognition objects in the subject below the vibrators 210 (on the −Z direction side), and reflectors 40, 41 are observed. The area and shape of the cross section (XZ plane) of the short axis direction of reflectors 40 and 41 are assumed to be the same.

In step S13 of the first three-dimensional image display processing, the B-mode image data of the vibrator VA containing the reflector image of the reflector 40 is generated. The brightness of each of these pixels is set to brightness a1. B-mode image data of vibrator VB including reflector images of reflectors 40 and 41 is generated in step S15. The brightness of each of these pixels is set to brightness b1. B-mode image data of vibrator VC including reflector images of reflector 40 is generated in step S17. The brightness of each of these pixels is set to brightness c1.

In step S19, as shown in FIG. 12C, B-mode image data of vibrators VC, VB, and VC are combined (added) so that the brightness of each pixel becomes brightness b2 in the following formula (1), to generate the three-dimensional image data of three-dimensional image I62 as pseudo three-dimensional image.

$$b2 = 3b1 - (a1 + c1) \tag{1}$$

The three-dimensional image I62 includes the reflector image I402 of the reflector 40 and reflector image I412 of reflector 41. If the second three-dimensional image generation method is used to generate a three-dimensional image from reflectors 40 and 41 in FIG. 12A, three-dimensional image data for three-dimensional image I61 including reflector image I401 of reflector 40 and reflector image I411 of reflector 41 shown in FIG. 12B is generated.

In the three-dimensional image I61, displaying is made similarly whether the reflector is long (reflector 40) or short (reflector 41) in the short axis direction. Thus, it is difficult to identify the shape of a tumor or other reflector. In contrast, for three-dimensional image I62, the longer the short axis direction is, the lower the brightness is, which makes it easier to grasp the shape of the reflector. In addition, when acquiring the ultrasound image while sliding the ultrasound probe 2 in the short axis direction, a short reflector in the short axis direction is not easily missed.

Description is made for a specific example of the seventh three-dimensional image generation method of the first three-dimensional image display processing with reference to FIG. 13A through FIG. 13D. Here, description is made for an example using the seventh three-dimensional image generation method of generating the three-dimensional image data of three-dimensional image as pseudo three-dimensional image by coloring and adding for the B-mode images respectively corresponding to the vibrators VA, VB, VC of ultrasound probe 2, as the three-dimensional image generation method of the first three-dimensional image display processing.

The seventh three-dimensional image generation method also uses the ultrasound diagnostic device 100 to perform similar processing to the first three-dimensional image display processing in FIG. 6, but steps S11, S14, S16, S18 and S21 are assumed not to be performed.

As shown in FIG. 13A, there is considered a case where, when looking at the ultrasound probe 2 in FIG. 3 from the +Z direction, reflector 42 is located as recognition object in the subject below the vibrators 210 (on the −Z direction side), and the reflector 42 is observed. The brightness of the reflector 42 is uniform.

In step S13 of the first three-dimensional image display processing, the B-mode image data of the vibrator VA is generated, and in step S19, the reflector image of the reflector 42 is colored with the color corresponding to the vibrator VA (for example, red), to generate the colored B-mode image data for the vibrator VA. The reflector image of reflector 42 is not contained in the B-mode image data of vibrator VA.

As shown in FIG. 13B, B-mode image data for vibrator VB is generated in step S15, and in step S19, the reflector image I421 of reflector 42 is colored with a color corresponding to the vibrator VB (e.g., blue (the "grid pattern" on the figure), to generate B-mode image data of colored B-mode image IB5 for vibrator VB. As shown in FIG. 13C, B-mode image data for vibrator VC is generated in step S17, and in step S19, the reflector image I422 of reflector 42 is colored with a color corresponding to the vibrator VC (e.g., green (the "shaded pattern (hatching)" on the figure), to generate B-mode image data of colored B-mode image IC5 for vibrator VC.

As shown in FIG. 13D, in step S19, the B-mode image data of vibrator VA, B-mode image data of B-mode image IB5 and the B-mode image data of B-mode image IC5 are combined (added) to generate three-dimensional image data of the three-dimensional image I7 as pseudo three-dimensional image of B-mode. Three-dimensional image I7 of B-mode includes reflector image I422 and reflector image I423. The reflector image I423 is a composite part of the reflector image I421 and the reflector image I422, and its color is also an added color (in this case, blue+green, which is blue-green). In step S20, the three-dimensional image I7 of B-mode is displayed on the display 16.

This allows the shape of the reflector 42 as the recognition object to be depicted three-dimensionally by separating the colors for each row of the short axis. By observing the three-dimensional image I7 of the B-mode, the operator can easily grasp the overall image of the reflector 42 in the short axis direction. In particular, the operator can easily grasp the portions across the short axis rows by the added colors of the rows. For example, the shape of a tumor or other object as a reflector in the subject can be easily grasped, facilitating the detection of lesions.

As a configuration different from the above coloring configuration, in step S19, the color corresponding to the vibrators VA, VB (e.g., purple) may be applied to the portion where the difference between the brightness value of the B-mode image data of vibrator VA and the brightness value of the B-mode image data of vibrator VB adjacent to vibrator VA in the short axis direction exceeds a predetermined threshold value set in advance for the pixel at the same position of vibrators VA, VB, VC, and the color corresponding to vibrators VB and VC (different from the color corresponding to vibrators VA and VB, e.g., blue-green) may be applied to the portion where the difference between the brightness value of the B-mode image data of vibrator VB and the brightness value of the B-mode image data of vibrator VC adjacent to vibrator VB in the short axis direction exceeds a predetermined threshold value set in advance, to generate the three-dimensional image data obtained by combining (adding) three pieces of B-mode image data.

Referring to FIG. 14A through FIG. 14C, the case for generating and displaying color flow image data in color Doppler mode is described.

In the case of generating and displaying color flow image data, the controller 11 of the ultrasound diagnostic device 100 also performs similar processing to the first three-dimensional image display processing in FIG. 6. However, the ROI is input by the operator via the operation input interface 17 in advance, and in step S12, the drive signals for color flow image data generation in the input ROI and B-mode image data generation are input to the vibrators VA, VB and VC. In steps S13, S15, and S17, under the control of the controller 11, the image generator 14 generates B-mode image data and color flow image data for the frame of same time for each of the vibrators VA, VB, and VC. In steps S14, S16, and S18, the brightness of the color flow image data and B-mode image data are adjusted.

In step S19, corresponding to each of the vibrators VA, VB, and VC, the brightness-adjusted color flow image data is combined (added) to generate three-dimensional image data and the brightness-adjusted B-mode image data is combined (added) to generate three-dimensional image data. In step S20, a composite image of the generated image data of the generated color flow image and the generated image data of the generated B-mode image is displayed on the display 16.

In steps S12 through S18, only B-mode image data in which the brightness of one row of vibrators (e.g., vibrator VB) is adjusted may be configured to be generated. In this case, three-dimensional image data of the color flow image is generated in step S19. In step S20, the three-dimensional image data of the color flow image and the B-mode image data of the single row of vibrators are superimposed on the display 16.

The first to the seventh three-dimensional image generation methods are applicable to the first three-dimensional image display processing for color flow image data generation and display, similarly to the first three-dimensional image display processing for B-mode image data generation and display. The B-mode image or color flow image in the seventh three-dimensional image generation method may be colored by colors other than those indicating blood flow velocity (red and blue) in the color flow image.

Here, description is made for a specific example of using the second three-dimensional image generation method in the first three-dimensional image display processing for generating and displaying the color flow image data. As shown in FIG. 14A, as the subject, silicon tube with a liquid flowing through its hollow part, which is a recognition object that imitates a blood vessel is scanned. This silicone tube consists of two silicone tubes arranged in a spiral shape. Such spiral vessels are seen, for example, in the umbilical cord blood vessels of a fetus.

With the second three-dimensional image generation method of the first three-dimensional image display processing, the silicon tube is scanned, and as shown in FIG. 14C, three-dimensional image data of the composite image I72 is generated and displayed on the display 16. The composite image I72 includes three-dimensional image I721 of the color flow image within ROIR1 and three-dimensional image of the B-mode image within and outside ROIR1. In FIG. 14B and FIG. 14C, the blue areas of the color flow image (where the fluid is flowing away from the ultrasound probe 2) are represented by a "grid pattern" and the red areas (where the fluid is flowing toward the ultrasound probe 2) is represented by a "shaded pattern".

As shown in FIG. 14B, in composite image 171 which has only B-mode image and color flow image I711 in ROIR1 corresponding to vibrator VB being superimposed, the structure of the silicon tube as a recognition object is difficult to understand. In contrast, the composite image I72 allows the operator to observe the silicon tube so that the structure of the silicon tube as the recognition object can be seen, along with the state of fluid flow.

As described above, according to the embodiment, the ultrasound diagnostic device 100 includes: an ultrasound probe 2 including multiple vibrators 210 that are arrayed to be multiple rows a, b, c in the long axial direction arranged in the short axis direction and that transmit and receive ultrasonic waves and switching elements 230 that switch on and off of input of drive signals to the vibrators in rows a, b, c and output of received signals; an image generator 14 that generates ultrasound image data (B-mode image data, color flow image data) of the tomographic plane for each of the rows a, b, c on the basis of the received signal received by the vibrator VA, VB, VC corresponding to each of the rows a, b, c via the switching of switching element 230; and a three-dimensional image generator 15 that generates three-dimensional image data from the generated ultrasound image data of the multiple rows.

Therefore, three-dimensional image data with the ultrasound image of the appropriate position in the depth direction (short axis direction) can be generated, and the operator can easily recognize the three-dimensional structure of the recognition object by observing the three-dimensional image data.

The image generator 14 generates ultrasound image data of the color flow image for each of the rows a, b, c on the basis of the received signal received by the vibrators VA, VB, VC corresponding to each of the rows a, b, c via the switching of switching element 230. Therefore, the operator can easily recognize the three-dimensional structure of blood flow and blood vessels as recognition objects by observing the three-dimensional image data of the color flow image.

In the first three-dimensional image generation method, the ultrasound diagnostic device 100 includes an operation input interface 17 that receives an input of the viewpoint of the three-dimensional image data. The three-dimensional image generator 15 adjusts the brightness of ultrasound image data to be lower for a row with a longer distance from the input viewpoint, and generates the three-dimensional image data from the ultrasound image data of the multiple rows a, b, c having the brightness adjusted. Therefore, simple three-dimensional image data can be composed, and the operator can easily recognize the positional relationship of the short axis direction of the recognition object by observing the brightness of the three-dimensional image data.

In the second three-dimensional image generation method, the three-dimensional image generator 15 combines the generated ultrasound image data for the multiple rows a, b, c without changing the ultrasound image data of the multiple rows a, b, c, to generate the three-dimensional image data. This makes it possible to compose simple three-dimensional image data, enabling the operator to grasp the overall image of the short axis direction of the recognition object by observing the three-dimensional image, and reducing the processing burden of brightness adjustment.

In the third three-dimensional image generation method, the three-dimensional image generator 15 generates three-dimensional image data by selecting the pixel with the maximum brightness among the pixels at the same position of the generated ultrasound image data of the multiple rows a, b, c. Therefore, simple three-dimensional image data can be composed, and recognition objects with partially high brightness in the short axis direction can be clearly depicted and recognized.

In the fourth three-dimensional image generation method, the three-dimensional image generator 15 generates three-dimensional image data by selecting the pixel on which superimposing is to be performed when the brightness difference between the brightness value of pixel on which superimposing is to be performed and the brightness value of the pixel to be superimposed among the pixels at the same position of the generated ultrasound image data for the multiple rows a, b, c exceeds a predetermined first threshold value. Therefore, simple three-dimensional image data can be composed, and the operator can use the three-dimensional image data to accurately recognize, for example, a recognition object with a portion that is far away from the viewpoint position in the short axis direction.

In the fifth three-dimensional image generation method, the three-dimensional image generator 15 generates three-dimensional image data of an image with a three-dimensionality corresponding to the input viewpoint from the generated ultrasound image data of the multiple rows a, b, c. Therefore, the operator can easily and accurately recognize the recognition object by the three-dimensional shape, and the positional relationship of the object in the subject can be recognized more clearly by changing the viewpoint position and observing it.

In the sixth three-dimensional image generation method, the three-dimensional image generator 15 generates three-dimensional image data by increasing the brightness for a larger change amount of brightness in the short axis direction for the pixels at the same position of the generated ultrasound image data for the multiple rows a, b, c by the formula (1), for example. This makes it possible to compose simple three-dimensional image data, facilitating the operator's grasp of the shape of recognition objects with different lengths in the short axis direction, for example, by means of the three-dimensional image I62, and also making it difficult to miss recognition objects that are short in the short axis direction when acquiring the ultrasound images with the ultrasound probe 2 sliding in the short axis direction.

In the seventh three-dimensional image generation method, the three-dimensional image generator 15 generates the three-dimensional image data by performing different coloring to the generated ultrasound image data for each of the rows a, b, c or by performing different coloring to a pixel for which a brightness difference for each two adjacent rows among all the rows exceeds a predetermined second threshold value for the pixels at the same position of the ultrasound image data of the respective rows a, b, c. This makes it possible to construct simple three-dimensional image data, and to depict the shape of the recognition object three-dimensionally by separating the colors for each of the short axis rows a, b, and c. By observing the three-dimensional image data, the operator can easily recognize the overall image of the recognition object in the short axis direction, and in particular, the portion across the rows in the short axis direction can be easily recognized by the added color of each row.

Second Embodiment

Figure 15:
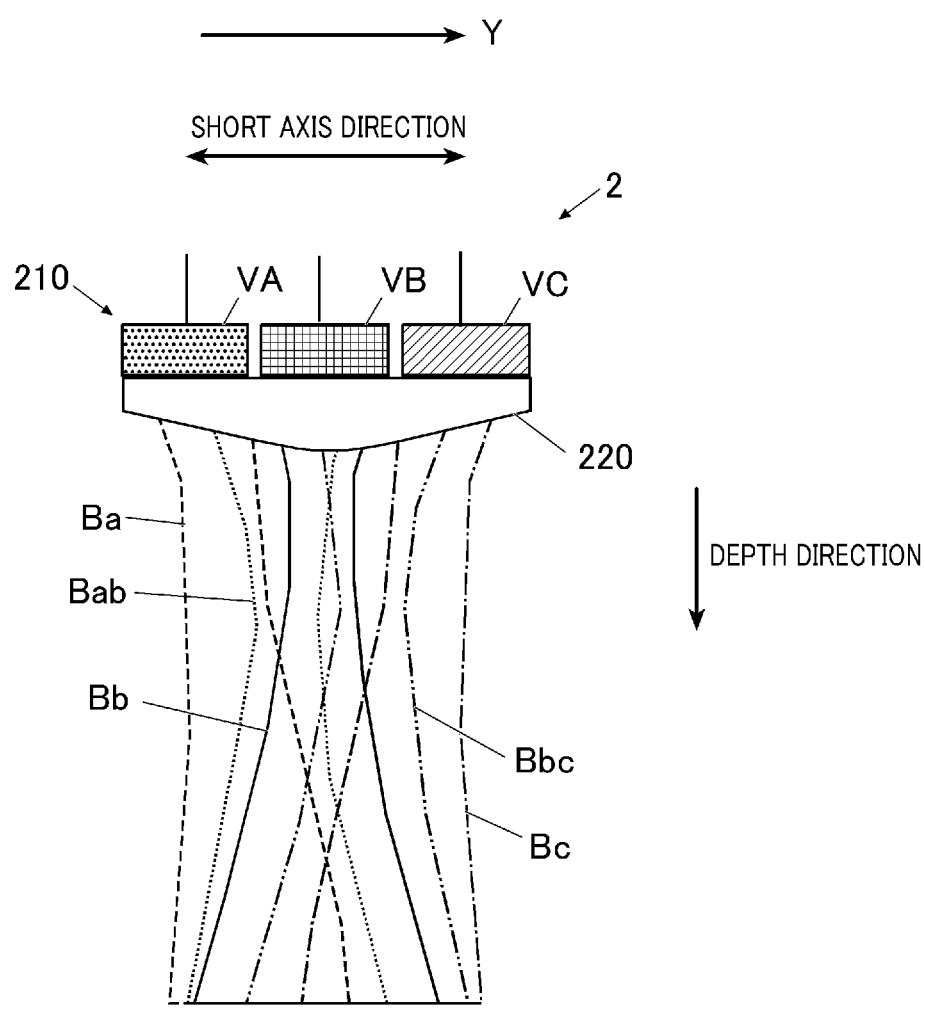
FIG. 15 is a view showing the schematic configuration and five ultrasonic beams in the short axis direction of ultrasound probe in the second embodiment.
Figure 16:
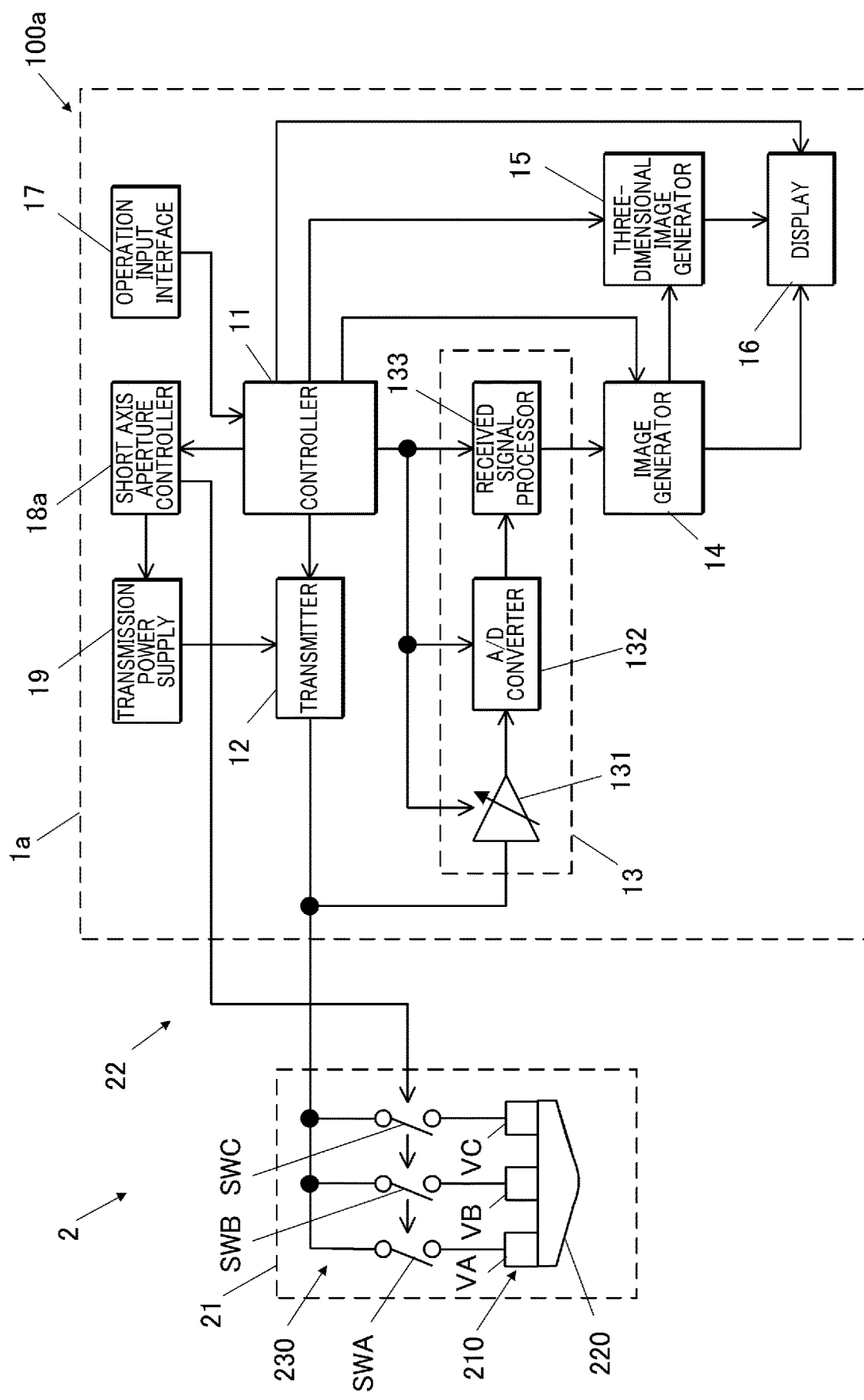
FIG. 16 is a block diagram showing the internal configuration of the ultrasound diagnostic device in the second embodiment.
Figure 17:
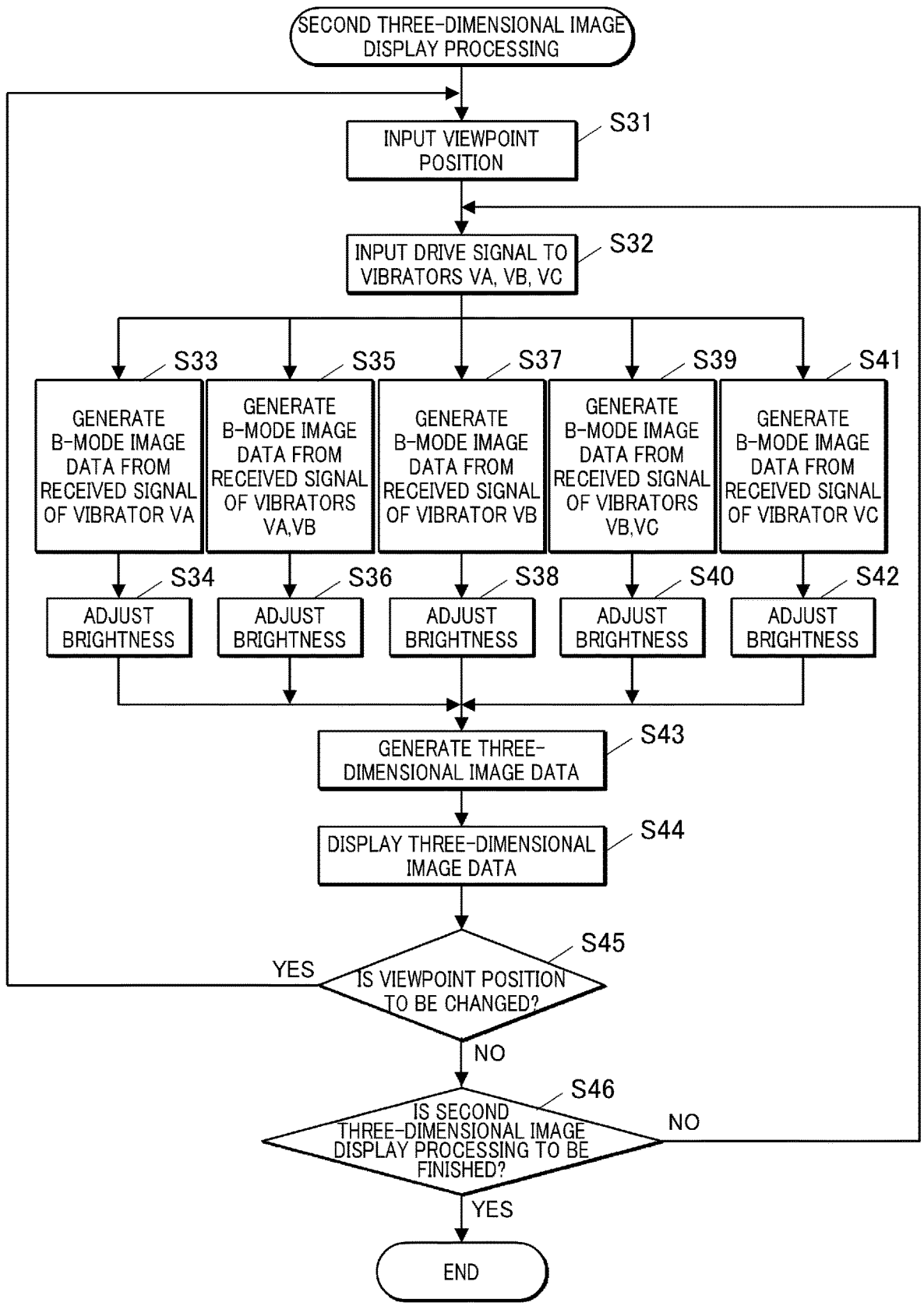
FIG. 17 is a flowchart showing the second three-dimensional image display processing.

With reference to FIGS. 15 to 17, the second embodiment according to the present invention will be described. First, with reference to FIGS. 15 and 16, the device configuration in the embodiment will be described. FIG. 15 shows the schematic configuration of the ultrasound probe 2 in the short axis direction of the embodiment and the five ultrasonic beams Ba, Bb, Bc, Bab, and Bbc. FIG. 16 is a block diagram showing the internal structure of the ultrasound diagnostic device 100*a* in the embodiment.

In the first embodiment, the three-dimensional image data is generated by transmitting ultrasonic beams Ba, Bb, Bc from the respective vibrators VA, VB, VC which are the rows in the short axis direction of the vibrators 210 in the ultrasound probe 2 and generating the ultrasound image data (B-mode image data, color flow image data). When generating and displaying the three-dimensional image data by using the vibrators VA, VB, VC arranged in the short axis direction, if vibrators VA, VB, and VC are used individually for transmitting and receiving ultrasonic waves, the resolution in the depth direction (short axis direction) of the three-dimensional image is not much obtained. Thus, in the second embodiment, the three-dimensional image data is generated by transmitting, in addition to the ultrasonic beams Ba, Bb, Bc, ultrasonic beams simultaneously from two vibrators (vibrators VA, VB, vibrators VB, VC) adjacent in the short axis direction and generating the ultrasound image data.

As shown in FIG. 15, in the embodiment, in the vibrators VA, VB, VC of vibrators 210 in the ultrasound probe 2, the vibrator VA sends ultrasonic beam Ba to the subject and receives reflected ultrasonic waves from the subject, the vibrator VB sends ultrasonic beam Bb to the subject and receives reflected ultrasonic waves from the subject, and the vibrator VC sends ultrasonic beam Bc to the subject and receives reflected ultrasonic waves from the subject. In addition to this, two vibrators VA and VB adjacent to each other in the short axis direction send ultrasonic beam Bab to the subject and receive reflected ultrasonic waves from the subject, and two adjacent vibrators VB and VC in the short axis direction send ultrasonic beam Bbc to the subject and receive reflected ultrasonic waves from the subject. From the received signal of each of these reflected ultrasonic waves, the ultrasound image data is generated, respectively. Therefore, since the ultrasound image data can be generated from each of the vibrators VA, VB (ultrasonic beam Bbc), vibrators VB, VC (ultrasonic beam Bbc), the resolution in the depth direction (short axis direction) is improved by filling in the space between the ultrasound image data with vibrator VA, the ultrasound image data with vibrator VB, and the ultrasound image data with vibrator VC.

The vibrators VA, VB, VC and the acoustic lens 220 are configured such that the ultrasonic beams Ba, Bb, Bc do not overlap up to a predetermined depth and are located exclusively, but as shown in FIG. 15, the ultrasonic beam Bab overlaps with the ultrasonic beams Ba, Bb before reaching the predetermined depth, and the ultrasonic beam Bbc overlaps with the ultrasonic beams Bb, Bc before reaching the predetermined depth. For each ultrasonic beam position, ultrasonic beams Ba, Bab, Bb, Bbc, and Bc are located in order from the −Y direction to the +Y direction.

The embodiment uses the ultrasound diagnostic device 100*a* shown in FIG. 16 as the device configuration. In the ultrasound diagnostic device 100*a*, the same parts as in the ultrasound diagnostic device 100 of the first embodiment will be marked with the same symbols and their description will be omitted, and the different parts will be mainly described.

The ultrasound diagnostic device 100*a* includes the ultrasound probe 2. The ultrasound diagnostic device body 1*a* includes the controller 11, the transmitter 12, the receiver 13, the image generator 14, the three-dimensional image generator 15, the display 16, the operation input interface 17, the short axis aperture controller 18*a*, and a transmission power supply 19.

The HDD of the controller 11 stores a second three-dimensional image display program for performing the second three-dimensional image display processing described below, instead of the first three-dimensional image display program.

The short axis aperture controller 18*a* stores the setting information for the transmission/reception sequence of the vibrators 210 for transmitting and receiving ultrasonic waves over the short axis direction (FIG. 3) of a two-dimensional array of the vibrators 210. The short axis aperture controller 18*a* switches on/off the switching elements 230 corresponding to the respective vibrators 210 according to the setting information and controls the power supply voltage of the transmission power supply 19 according to the control of the controller 11. The transmission power supply 19 is the power supply, which outputs the power supply power of the controlled supply voltage to the transmitter 12 for the drive signal according to the control of the short axis aperture controller 18*a*.

As shown in FIG. 15, in the case where ultrasonic waves are transmitted and received with a single row a, b, c of vibrators in the short axis direction (each of vibrators V A, VB, and VC) and ultrasonic waves are transmitted and received with two adjacent rows of vibrators (vibrators VA, VB, or vibrators VB, VC) in the short axis direction, when comparing the amplitudes of the signals transmitted and received by only the vibrators in the single rows a, b, and c in the short axis direction with the amplitudes of the signals transmitted and received by the two adjacent rows of vibrators in the short axis direction, the signal amplitude is larger when two adjacent rows of vibrators in the short axis direction are used. This is because using the two rows of vibrators increases the vibrator area and thus the output of transmitted pulse is large and more ultrasonic wave energy can be collected when the ultrasonic waves are received.

In the case where the magnitude of the received signal differs when only a single row of vibrators a, b, and c in the short axis direction is used, and when two adjacent rows of vibrators in the short axis direction are used in such a way, defects may occur when ultrasound image data is generated. As an example, when the B-mode image of the tomographic plane that is farther away from the operator's viewpoint position in the short axis direction is displayed darker (lower brightness) (the first three-dimensional image generation method), The desired effect is not achieved because of the difference in signal brightness. One solution to this problem is to adjust the gain of the signal.

To be specific, when transmitting and receiving ultrasonic waves with two adjacent rows of vibrators in the short axis direction, the short axis aperture controller 18*a* controls the transmission power supply 19 to output the power supply voltage smaller than the power supply voltage for transmitting and receiving ultrasonic waves with the single row a, b, c of vibrators in the short axis direction, and causes the transmitter 12 to generate a drive signal whose drive voltage is adjusted to be smaller by the power supply voltage. At this time, when transmitting and receiving ultrasonic waves with two adjacent rows of vibrators in the short axis direction, the gain of the received signal is not adjusted compared to transmitting and receiving ultrasonic waves with the single row a, b, c of vibrators. With this configuration, the increase in amplitude of the received signal voltage in the case of ultrasonic wave transmission and reception of two adjacent rows of vibrators in the short axis direction is appropriately corrected by controlling the drive signal voltage with the short axis aperture controller 18a.

With reference to FIG. 17, the operation of the ultrasound diagnostic device 100a will be described. FIG. 17 is the flowchart showing the second three-dimensional image display processing.

The second three-dimensional image display processing is the same as the first three-dimensional image display processing of the first embodiment, and performs live display of the three-dimensional image of the B-mode of the subject for the operator, such as a physician, to check the puncture needle 3 in the subject, the subject's tissue, etc. as the recognition object. Here, description is made for an example of applying the first three-dimensional image generation method described in the first three-dimensional image display processing to the second three-dimensional image display processing.

In the ultrasound diagnostic device 100, for example, in response to a trigger of accepting various setting information such as the frame rate of the first three-dimensional image display processing and instructions for executing the first three-dimensional image display processing from the operator via the operation input interface 17, the controller 11 executes the second three-dimensional image display processing in accordance with the second three-dimensional image display program stored in the HDD.

As shown in FIG. 17, step S31 is same as step S11 of the first three-dimensional image display processing. The controller 11 causes the transmitter 12 to generate drive signals corresponding to the ultrasonic beams Ba, Bab, Bb, Bbc, and Bc according to the various setting information input. At this time, via the short axis aperture controller 18a, the controller 11 regulates the voltage of the drive signal by the transmission power supply 19 performs the switching of the switching elements 230, and inputs the drive signals to the vibrators VA, VB, and VC to emit transmission ultrasonic waves and receive reflected ultrasonic waves (echoes) and causes the receiver 13 to generate received signals (step S32). As for the received signals obtained in step S32, the received signal for each frame at the same time corresponding to each of the vibrator VA, vibrator VA+vibrator VB, vibrator VB, vibrator VB+vibrator VC, and vibrator VC is acquired in order according to the transmission/reception sequence.

Steps S33, S37, and S41 are similar to steps S13, S15, and S17 of the first three-dimensional image display processing. The controller 11 causes the image generator 14 to generate one frame of B-mode image data from the received signals corresponding to the vibrators VA and VB generated by the receiver 13 in step S12 according to the various setting information input (step S35). In response to the various setting information input, the controller 11 causes the image generator 14 to generate one frame of B-mode image data from the received signals corresponding to the vibrators VB and VC generated by the receiver 13 in step S12 (step S39).

Steps S34, S38, and S42 are similar to steps S14, S16, and S18 of the first three-dimensional image display processing. After step S35, the controller 11 adjusts the brightness (brightness value) of the pixels in the B-mode image data generated in step S35 according to the distance from the viewpoint position input in step S11 to the position between vibrators VA and VB (ultrasonic beam Bab) (step S36). After step S39, the controller 11 adjusts the brightness (brightness value) of the pixels in the B-mode image data generated in step S39 according to the distance from the viewpoint position input in step S11 to the position between the vibrators VB and VC (ultrasonic beam Bbc) (step S40). In steps S34, S36, S38, S40, and S42, for example, for pixels of the same brightness, the brightness of the pixel in each B-mode image data is adjusted so that the one closest to the viewpoint position has the highest brightness, and the further away the pixel is, the lower the brightness becomes, for B-mode image data corresponding to vibrator VA in step S33, B-mode image data corresponding to vibrators VA and VB in step S35, B-mode image data corresponding to vibrator VB in step S37, vibrator B-mode image data corresponding to the vibrators VB, VC, in step S39, and B-mode image data corresponding to vibrator VC in step S41.

The controller 11 uses the three-dimensional image generator 15 to combine (add) the five pieces of B-mode image data of the same time frame whose brightness was adjusted in steps S34, S36, S38, S40, and S42, and generates the B-mode three-dimensional image data for one frame (step S43). Steps S44 to S46 are similar to steps S20 to S22 of the first three-dimensional image display processing.

The second to the seventh three-dimensional image generation methods can be applied to the second three-dimensional image display processing, similarly to the first three-dimensional image display processing. The second three-dimensional image display processing can be configured to display color flow image data similarly to the first three-dimensional image display processing. Specifically, in step S32, drive signals for B-mode image data and color flow image data are input to vibrators VA, VB, and VC. In steps S33, S35, S37, S39, and S41, the image generator 14 generates B-mode image data and color flow image data, and in steps S43 and 44, the B-mode three-dimensional image data and the three-dimensional image data of color flow image are generated and combined to be displayed on the display 16.

As described above, according to the embodiment, in the ultrasound diagnostic device 100a, the image generator 14 generates the ultrasound image data for adjacent two rows on the basis of the received signals received by the vibrators of adjacent two rows (a+b, b+c) among the multiple rows a, b, c via the switching of switching elements 230, in addition to the ultrasound image data of each of the rows a, b, c. The three-dimensional image generator 15 generates the three-dimensional image data from the ultrasound image data for the multiple rows a, b, c and the ultrasound image data for adjacent two rows (a+b, b+c). Thus, the resolution in the depth direction (short axis direction) of three-dimensional image data can be increased.

First Modification Example

Figure 18:
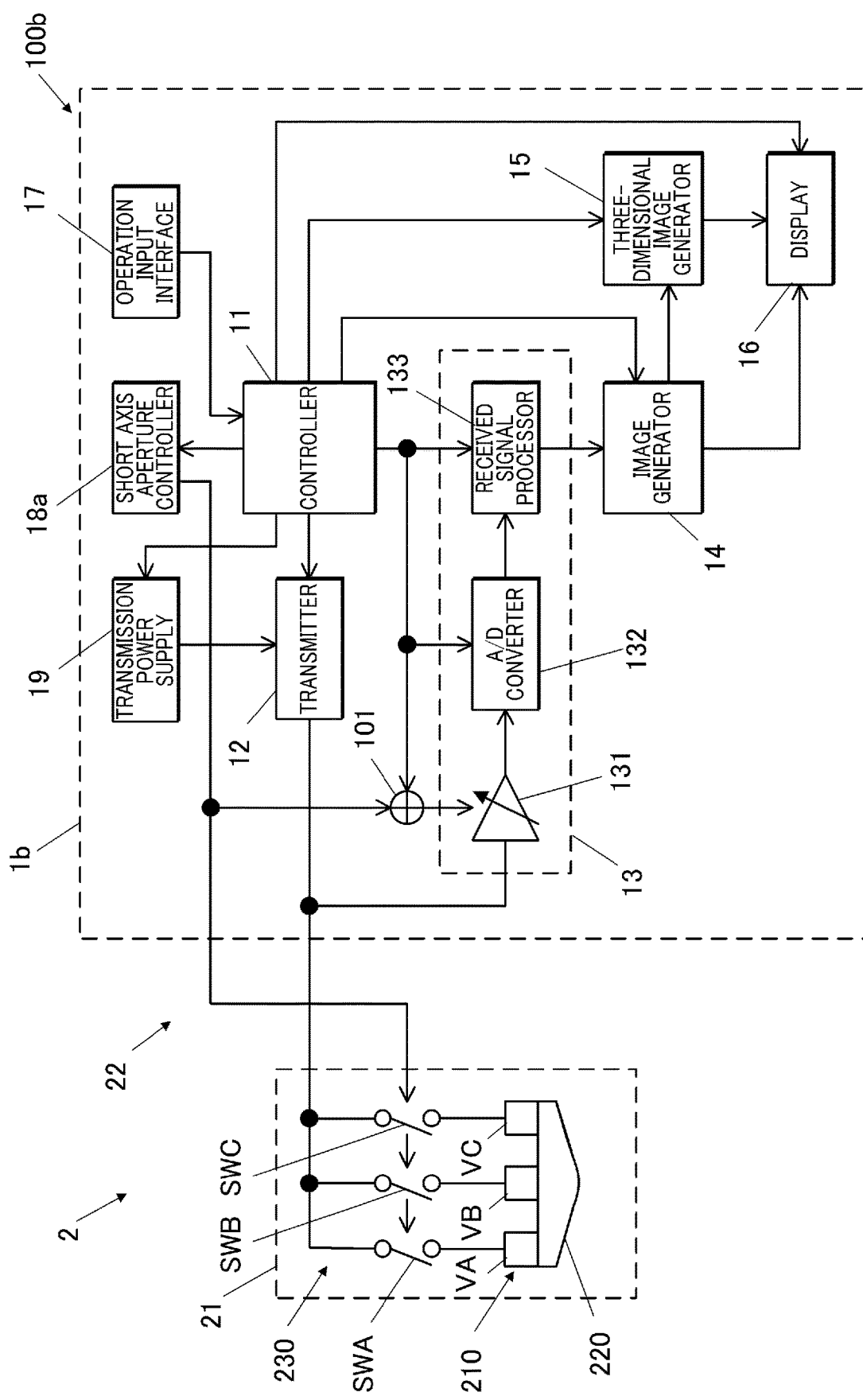
FIG. 18 is a block diagram showing the internal configuration of the ultrasound diagnostic device in a first modification example.

With reference to FIG. 18, a first modification example in the second embodiment will be described. FIG. 18 is a block diagram showing the internal configuration of the ultrasound diagnostic device 100b in the modification example.

In this modification example, as the device configuration, the ultrasound diagnostic device 100a in the second embodiment is replaced by the ultrasound diagnostic device 100b shown in FIG. 18. For the same parts in the ultrasound diagnostic device 100b as those in the ultrasound diagnostic device 100, 100a of the first and the second embodiment, the same symbols are used to omit their explanation, and the different parts are mainly explained.

The ultrasound diagnostic device 100b includes an ultrasound diagnostic device body 1b and the ultrasound probe 2. The ultrasound diagnostic device body 1b includes the controller 11, the transmitter 12, the receiver 13, the image generator 14, the three-dimensional image generator 15, the display 16, the operation input interface 17, the short axis aperture controller 18a, the transmission power supply 19, and an addition section 101.

The transmission power supply 19 outputs the power supply power for the drive signal generation to the transmitter 12 in accordance with the control of the controller 11. The addition section 101 is an adder that adds the control signals for opening and closing the switching elements 230 from the short axis aperture controller 18a and the control signal from the controller 11, and outputs them to the variable gain amplifier 131 of the receiver 13.

In the second embodiment, the short axis aperture controller 18a adjusts the voltage of the drive signal as gain adjustment of signals for preventing the amplitude of the voltage of the received signal from increasing when using two adjacent rows of vibrators (vibrators VA, VB, or vibrators VB, VC) in the short axis direction, compared to using only single row a, b, c vibrators (each of vibrators VA, VB, and VC) in the short axis direction. In this modification example, as gain adjustment of this signal, the voltage of the drive signal is not adjusted, but the gain of the received signal is adjusted. Specifically, the variable gain amplifier 131 amplifies the received signal input from the ultrasound probe 2 so that gain when using two adjacent rows of vibrators in the short axis direction is lower than gain when using only single row a, b, c vibrators in short axis direction according to the control signal input from the addition section 101. With this configuration, the increase in amplitude of the received signal voltage in the case of transmission and reception of ultrasonic waves by two adjacent rows of vibrators in the short axis direction is appropriately corrected by adjusting the gain of the received signal through control of the controller 11 and the short axis aperture controller 18a.

As described above, according to the modification example, the similar effect to that of the ultrasound diagnostic device 100a in the second embodiment is achieved.

Second Modification Example

Figure 19:
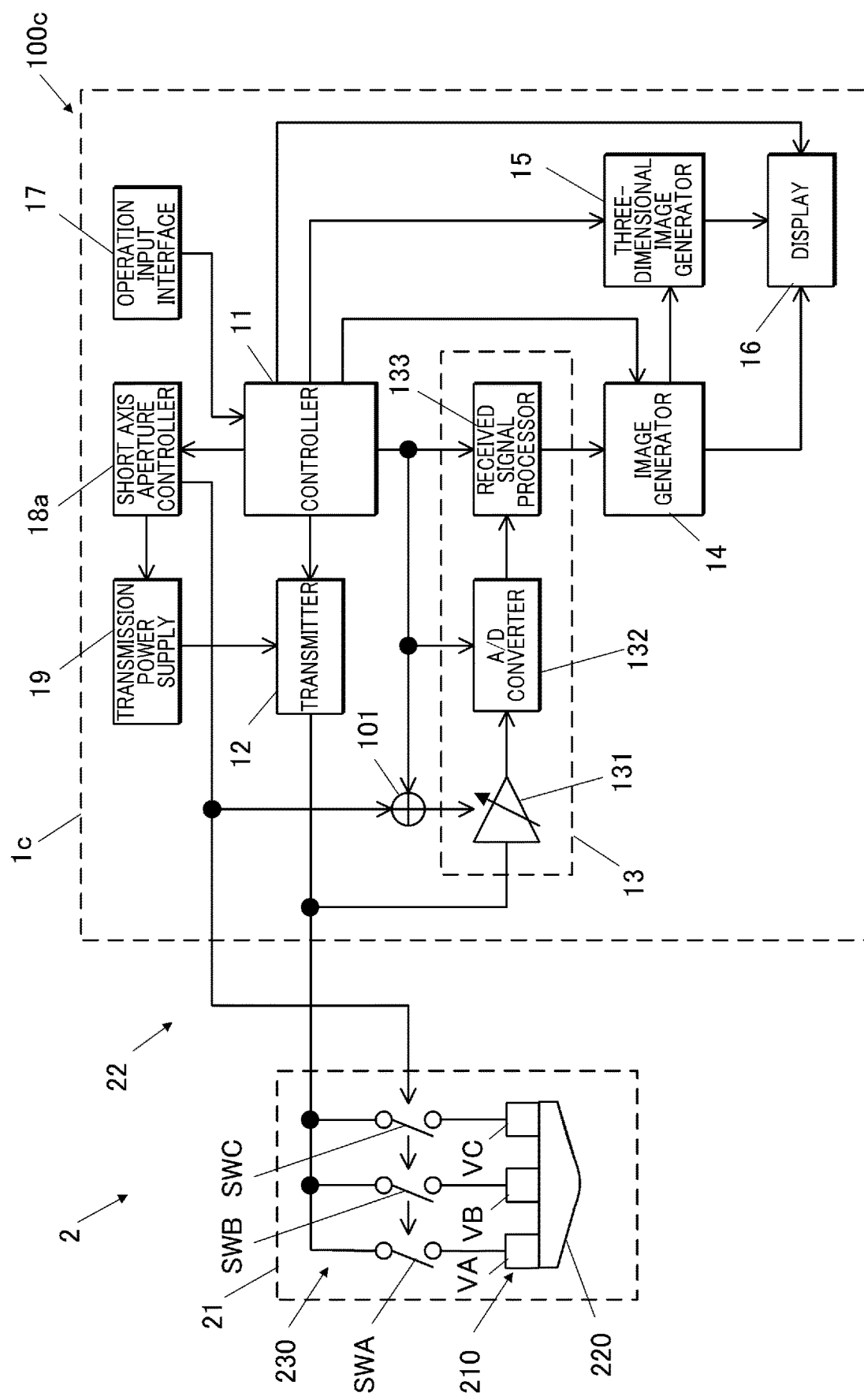
FIG. 19 is a block diagram showing the internal configuration of the ultrasound diagnostic device in a second modification example.

With reference to FIG. 19, the second modification example in the second embodiment will be described. FIG. 19 is a block diagram showing the internal configuration of the ultrasound diagnostic device 100c in the modification example.

In this modification example, as the device configuration, the ultrasound diagnostic device 100a in the second embodiment is replaced by the ultrasound diagnostic device 100b shown in FIG. 18. For the same parts of the ultrasound diagnostic device 100b as those in the ultrasound diagnostic device 100, 100a of the first and the second embodiment, the same symbols are used to omit their explanation, and the different parts are mainly explained.

The ultrasound diagnostic device 100c includes an ultrasound diagnostic device body 1c and the ultrasound probe 2. The ultrasound diagnostic device body 1c includes the controller 11, the transmitter 12, the receiver 13, the image generator 14, the three-dimensional image generator 15, the display 16, the operation input interface 17, the short axis aperture controller 18a, the transmission power supply 19, and the addition section 101.

In the second embodiment, the short axis aperture controller 18a adjusts the voltage of the drive signal as gain adjustment of signals for preventing the amplitude of the voltage of the received signal from increasing when using two adjacent rows of vibrators (vibrators VA, VB, or vibrators VB, VC) in the short axis direction, compared to using only single row a, b, c vibrators (each of vibrators VA, VB, and VC) in the short axis direction. In this modification example, as gain adjustment of this signal, the voltage of the drive signal is adjusted similarly to the second embodiment, and the gain of the received signal is adjusted similarly to the first modification example. Specifically, the short axis aperture controller 18a controls the power supply voltage of the power supply of the transmission power supply 19 when using two adjacent rows of vibrators in the short axis direction to be lower than when using only a single row a, b, c of vibrators in the short axis direction. In addition, the variable gain amplifier 131 amplifies the received signal input from the ultrasound probe 2 so that gain when using two adjacent rows of vibrators in the short axis direction is lower than gain when using only single row a, b, c vibrators in short axis direction according to the control signal input from the addition section 101. With this configuration, the increase in amplitude of the received signal voltage in the case of transmission and reception of ultrasonic waves by two adjacent rows of vibrators in the short axis direction is appropriately corrected by adjusting the voltage of drive signal through control of the short axis aperture controller 18a and adjusting the gain of the received signal through control of the controller 11 and the short axis aperture controller 18a.

As described above, according to the modification example, the similar effect to that of the ultrasound diagnostic device 100a in the second embodiment is achieved.

Third Modification Example

The third modification example as a modification example of the first and second embodiments will be described. The first and second embodiments (first, second modification examples) have a configuration of displaying the generated three-dimensional image data alone by the first, second three-dimensional image display processing, whereas this modification example has a configuration of displaying normal ultrasound image data (B-mode image data, or B-mode image data and color flow image data) and three-dimensional image data side by side on the display screen.

Figure 20:
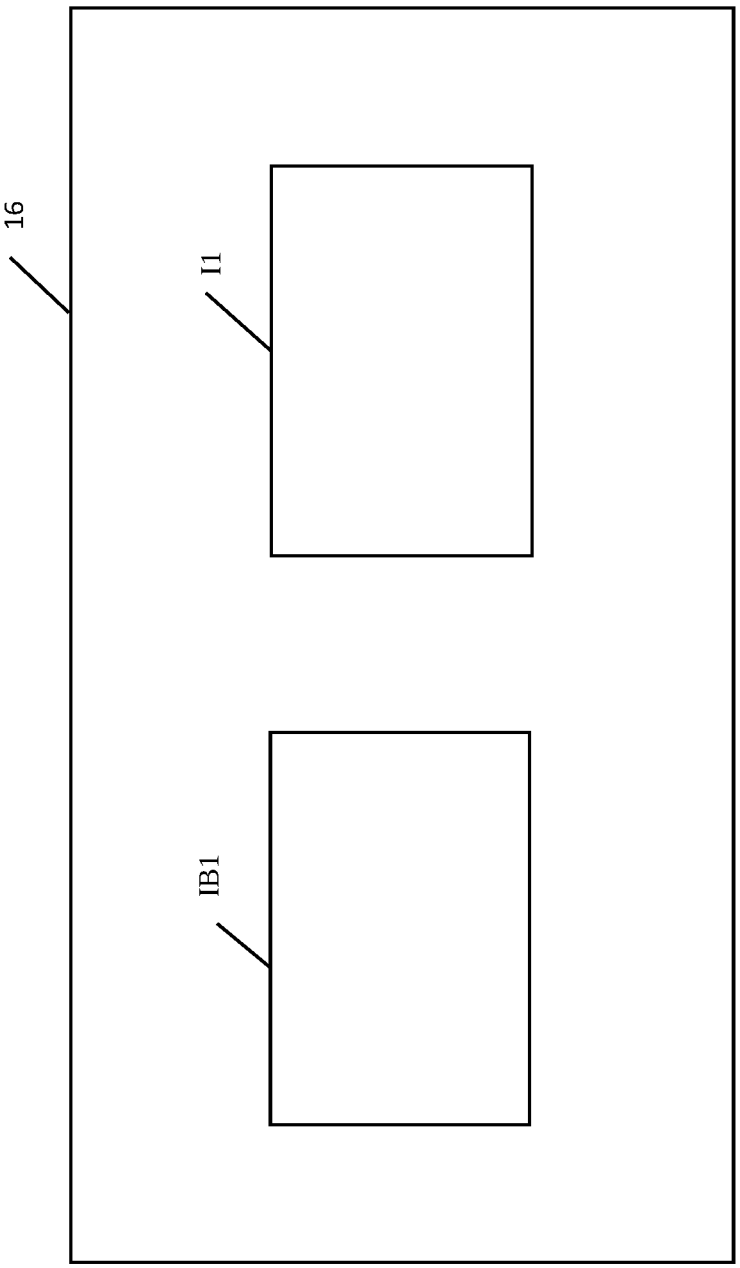
FIG. 20 is a schematic diagram of a display according to an embodiment of the present invention.

For example, in the first three-dimensional image display processing of FIG. 6 with the ultrasound diagnostic device 100, in step S20, by the controller 11, the normal B-mode image data IB1 corresponding to the vibrator VB generated in step S15 is placed at the left position in the display screen of the display 16, and the B-mode three-dimensional image data I1 generated in step S19 is placed at the right position in the display screen, to display these two pieces of image data side by side in the horizontal direction (See FIG. 20).

In the first three-dimensional image display processing of color Doppler mode, for example, in step S20, the composite image of the B-mode image data corresponding to the vibrator VB generated in step S15 and the color flow image data is placed at the left position in the display screen of the display 16, and the three-dimensional image data of color Doppler mode generated in step S19 (composite image of three-dimensional image data of B-mode and three-dimensional image data of color flow image) is placed at the right position in the display screen to display these two pieces of image data side by side in the horizontal direction.

The array position of image data in the display screen may be horizontally reversed for normal B-mode image data and three-dimensional image data, or the data may be arranged in the vertical direction, etc. The normal ultrasound image data and the three-dimensional image data can be displayed side by side on the display 16 also in the second three-dimensional image display processing in FIG. 17 by the ultrasound diagnostic devices 100a, 100b, 100c. The operator can easily compare the normal ultrasound image data with the three-dimensional image data visually.

As described above, according to the modification example, the ultrasound diagnostic device 100, 100a, 100b, 100c includes the controller 11 that displays the generated ultrasound image data and the generated three-dimensional image data side by side on the display 16. Thus, the operator can easily compare the normal ultrasound image data with the three-dimensional image data visually, and the ultrasound diagnostic device 100, 100a, 100b, 100c that is easier to use can be provided.

The above description discloses an example of using an HDD as a computer readable medium of program according to the present invention, but the medium is not limited to this example. As other computer readable medium, non-volatile memory such as ROM and flash memory, and portable recording media such as CD-ROM can be applied. Carrier wave is also applicable to the present invention as a medium to provide the data of the program according to the present invention via communication lines.

The description in the above embodiments and modification examples is an example of the ultrasound diagnostic device and program stored in the storage medium according to the present invention, and the present invention is not limited to this.

In the above embodiments and modification examples, by combining (synthesizing) the ultrasound images (ultrasound image data) created based on the received signals obtained in respective rows in the short axis direction of the vibrators 210 of the ultrasound probe 2, a single three-dimensional image (three-dimensional image data) is composed and displayed on the display 16. However, the display may be changed according to time. For example, when the three-dimensional image generator 15 performs a three-dimensional image display with the ultrasound image data for each row generated by the image generator 14, the three-dimensional image generator 15 performs the display by dividing time, such as by selecting and displaying only the ultrasound image at the far end of the depth direction (the row in the short axis direction of the vibrators 210 that is farthest back from the viewpoint position) at the first timing, displaying the three-dimensional image which is obtained by selecting and combining the two ultrasound images in the back two rows at the second timing, and displaying the three-dimensional image which is obtained by selecting and combining the ultrasound images in all the rows at the third timing, which allows the three-dimensional structure to be shown so as to be easier to understand. As for the display dividing time, the display may be performed by using the ultrasound image when the ultrasonic scanning is stopped (frozen), not during ultrasonic scanning In the above embodiments and modification examples, description is made for the ultrasound probe 2 having arrays of multiple vibrators in the longitudinal direction in the three rows in the short axis direction, but the ultrasound probe 2 is not limited to this. The number of divisions (number of vibrators) in the short axis direction may be increased, such as five rows, seven rows, etc. in the short axis direction.

As for the other detailed configurations and the detailed operations of devices forming the ultrasound diagnostic devices 100, 100a, 100b, 100c in the above embodiments and modification examples, changes can be made as needed within the scope of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:
1. An ultrasound diagnostic device comprising:
an ultrasound probe that includes:
multiple vibrators in a long axis direction and are arrayed to be multiple rows, the rows being arranged in a short axis direction, and that transmit and receive ultrasonic waves;
a switching element that switches on and off of input of a drive signal to a vibrator in each of the rows and output of a received signal;
an ultrasound image generator that generates ultrasound image data of a tomographic plane for each of the rows based on the received signal that is received by the vibrator corresponding to each of the rows via switching of the switching element; and
a three-dimensional image generator that generates three-dimensional image data from the generated ultrasound image data of the multiple rows,
wherein the three-dimensional image generator adjusts a brightness of the ultrasound image data to be lower for a row having a longer distance from a viewpoint position of a user, and generates three-dimensional image data from the ultrasound image data of the multiple rows having the brightness adjusted, the viewpoint position of the user being on a first side or a second side of the ultrasound probe, the first side and the second side being on opposing sides of the ultrasound probe in the short-axis direction.

2. The ultrasound diagnostic device according to claim 1, wherein the ultrasound image generator generates ultrasound image data of a color flow image for each of the rows based on the received signal that is received by the vibrator corresponding to each of the rows via the switching of the switching element.

3. The ultrasound diagnostic device according to claim 1, wherein
the ultrasound image generator generates, in addition to the ultrasound image data for each of the rows, ultrasound image data for two adjacent rows among the multiple rows based on received signals that are received by vibrators of the two adjacent rows via the switching of the switching element, and
the three-dimensional image generator generates three-dimensional image data from the ultrasound image data of the multiple rows and the ultrasound image data of the two adjacent rows that are generated.

4. The ultrasound diagnostic device according to claim 1, further comprising a hardware processor that displays the generated ultrasound image data and the generated three-dimensional image data side by side on a display.

5. The ultrasound diagnostic device according to claim 1, further comprising an operation input interface that receives input of the viewpoint position of the user, wherein the three-dimensional image generator generates the three-dimensional image data corresponding to the input viewpoint position from the generated ultrasound image data of the multiple rows.

6. The ultrasound diagnostic device according to claim 1, wherein the three-dimensional image generator generates three-dimensional image data by combining the generated ultrasound image data of the multiple rows without changing the ultrasound image data of the multiple rows.

7. The ultrasound diagnostic device according to claim 1, wherein the three-dimensional image generator generates three-dimensional image data by selecting a pixel with a maximum brightness among pixels at a same position in the generated ultrasound image data of the multiple rows.

8. The ultrasound diagnostic device according to claim 1, wherein the three-dimensional image generator generates three-dimensional image data by selecting a pixel on which superimposing is to be performed, in response to a brightness difference exceeding a predetermined first threshold value, the brightness difference being a difference between a brightness value of the pixel on which the superimposing is to be performed and a brightness value of a pixel to be superimposed among pixels at a same position in the generated ultrasound image data of the multiple rows.

9. The ultrasound diagnostic device according to claim 1, wherein the three-dimensional image generator generates three-dimensional image data of an image with a three-dimensionality from the generated ultrasound image data of the multiple rows.

10. The ultrasound diagnostic device according to claim 1, wherein the three-dimensional image generator generates three-dimensional image data by increasing a brightness in response to a brightness change amount in the short axis direction being larger for pixels at a same position in the generated ultrasound image data of the multiple rows.

11. The ultrasound diagnostic device according to claim 1, wherein the three-dimensional image generator generates three-dimensional image data by performing different coloring to the generated ultrasound image data for each of the rows, or by, for a pixel at a same position in the ultrasound image data of each of the rows, performing different coloring to a pixel for which a brightness difference for each two adjacent rows of all the rows exceeds a predetermined threshold value.

12. The ultrasound diagnostic device according to claim 1, wherein, in three-dimensional displaying by the generated ultrasound image data of each of the rows, the three-dimensional image generator performs different selection of an image to be used in displaying, according to time.

13. The ultrasound diagnostic device according to claim 1, wherein the three-dimensional image generator adjusts the brightness such that for pixels of a same brightness before the brightness is adjusted, a pixel in the row closest to the viewpoint position of the user has the highest brightness and pixels in rows that are further away from the viewpoint of the user have a lower brightness after the brightness is adjusted.

14. A non-transitory computer-readable storage medium storing a program for a computer of an ultrasound diagnostic device including an ultrasound probe that includes: multiple vibrators in a long axis direction are arrayed to be multiple rows, the rows being arranged in a short axis direction, and that transmit and receive ultrasonic waves; and a switching element that switches on and off of input of a drive signal to a vibrator in each of the rows and output of a received signal, the program causing the computer of the ultrasound diagnostic device to perform ultrasound image generating that is generating ultrasound image data of a tomographic plane for each of the rows based on the received signal that is received by the vibrator corresponding to each of the rows via switching of the switching element; and three-dimensional image generating that is generating three-dimensional image data from the generated ultrasound image data of the multiple rows, wherein the ultrasound image generating adjusts a brightness of the ultrasound image data to be lower for a row having a longer distance from a viewpoint position of a user, and generates three-dimensional image data from the ultrasound image data of the multiple rows having the brightness adjusted, the viewpoint position of the user being on a first side or a second side of the ultrasound probe, the first side and the second side being on opposing sides of the ultrasound probe in the short-axis direction.

* * * * *